United States Patent
Yokoyama

(10) Patent No.: US 10,153,061 B2
(45) Date of Patent: Dec. 11, 2018

(54) METAL GRATING FOR X-RAYS, PRODUCTION METHOD FOR METAL GRATING FOR X-RAYS, METAL GRATING UNIT FOR X-RAYS, AND X-RAY IMAGING DEVICE

(71) Applicant: KONICA MINOLTA, INC., Chiyoda-ku (JP)

(72) Inventor: Mitsuru Yokoyama, Takatsuki (JP)

(73) Assignee: KONICA MINOLTA, INC., Tokyo (JP)

( * ) Notice: Subject to any disclaimer, the term of this patent is extended or adjusted under 35 U.S.C. 154(b) by 90 days.

(21) Appl. No.: 15/025,174

(22) PCT Filed: Jul. 24, 2014

(86) PCT No.: PCT/JP2014/069517
§ 371 (c)(1),
(2) Date: Mar. 25, 2016

(87) PCT Pub. No.: WO2015/045596
PCT Pub. Date: Apr. 2, 2015

(65) Prior Publication Data
US 2016/0240276 A1    Aug. 18, 2016

(30) Foreign Application Priority Data
Sep. 26, 2013    (JP) .................................. 2013-199968

(51) Int. Cl.
*A61B 6/00*    (2006.01)
*G21K 1/06*    (2006.01)
(Continued)

(52) U.S. Cl.
CPC ................ *G21K 1/06* (2013.01); *A61B 6/484* (2013.01); *G01N 23/04* (2013.01);
(Continued)

(58) Field of Classification Search
None
See application file for complete search history.

(56) References Cited

U.S. PATENT DOCUMENTS

2012/0099706 A1*   4/2012   Kaneko .................... C25D 3/48
378/87
2013/0279651 A1   10/2013   Yokoyama

FOREIGN PATENT DOCUMENTS

JP    2012-093429    5/2012
JP    2012-150219    8/2012
(Continued)

*Primary Examiner* — Hoon Song
(74) *Attorney, Agent, or Firm* — Cozen O'Connor

(57)    ABSTRACT

An X-ray metal grating structure of the present invention has a grating region in which a plurality of first structural portions are periodically provided, wherein an air gap is formed between each of the plurality of first structural portions and a second structural portion as a remaining part of the grating region other than the plurality of first structural portions. Thus, the X-ray metal grating structure of the present invention is formed as a grating structure having high flatness. A production method therefor comprises a step of forming the air gap between the first structural portion and the second structural portion. Thus, the production method makes it possible to produce an X-ray metal grating structure having high flatness. The present invention further provides an X-ray metal grating unit and an X-ray imaging device each comprising the X-ray metal grating structure.

13 Claims, 16 Drawing Sheets

(51) Int. Cl.
    *G02B 5/18*     (2006.01)
    *G01N 23/04*    (2018.01)
    *G01N 23/20*    (2018.01)
(52) U.S. Cl.
    CPC ..... *G01N 23/20075* (2013.01); *G02B 5/1838*
            (2013.01); *A61B 6/4035* (2013.01); *A61B*
         *6/4291* (2013.01); *G01N 2223/064* (2013.01);
                                *G21K 2207/005* (2013.01)

(56)            References Cited

FOREIGN PATENT DOCUMENTS

JP      2013-049923    3/2013
WO    WO 2012/086121   6/2012

\* cited by examiner

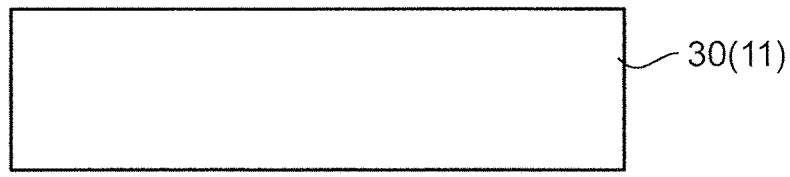
FIG.2A
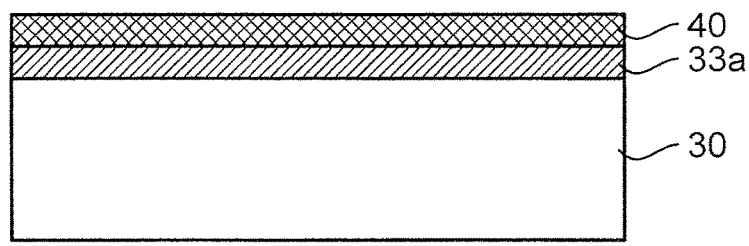
FIG.2B
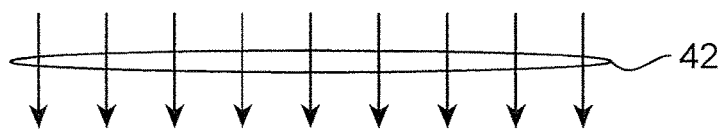
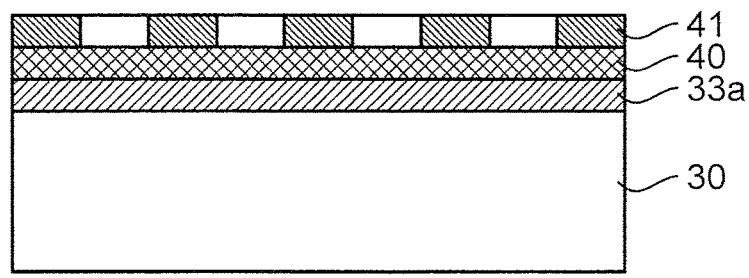
FIG.2C
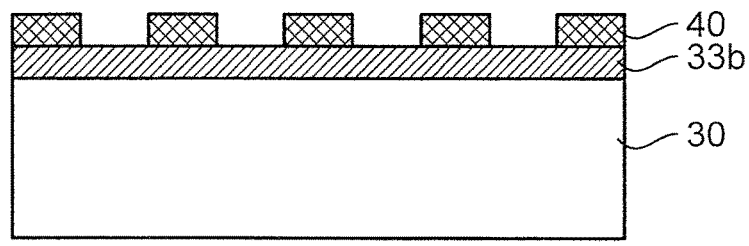
FIG.2D

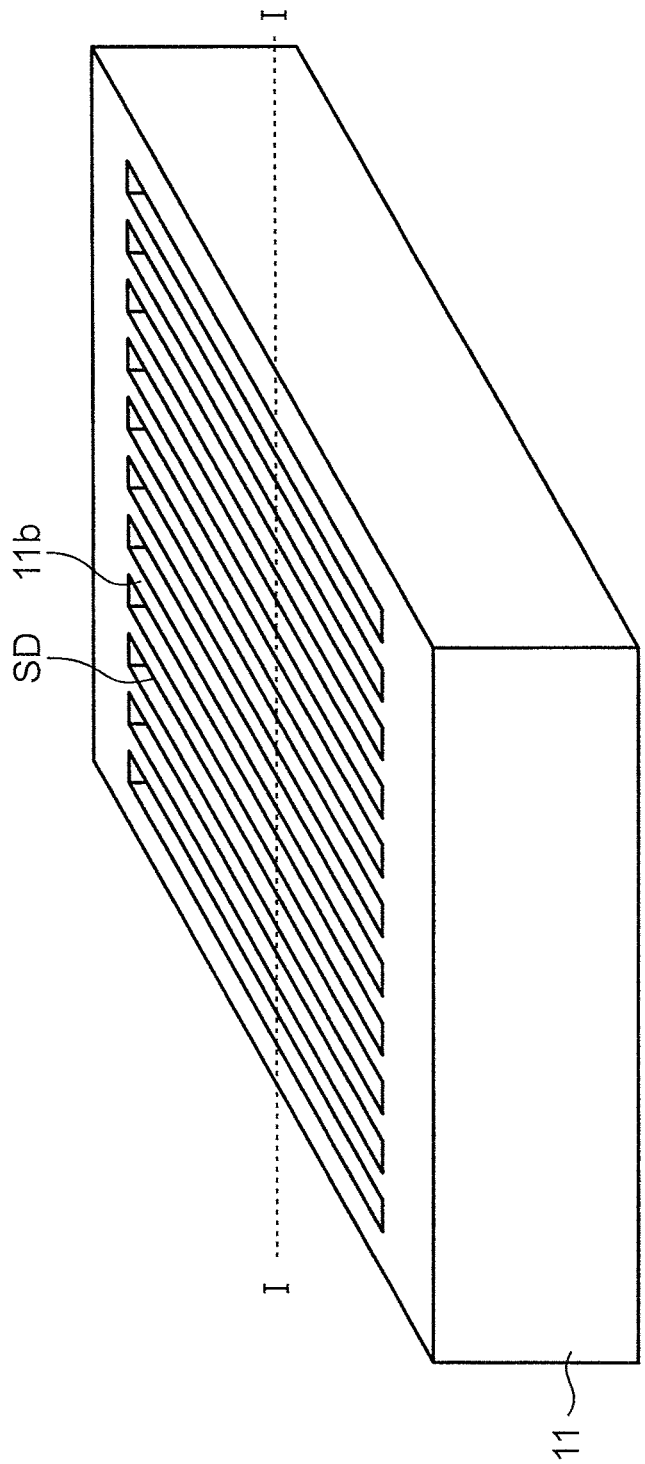

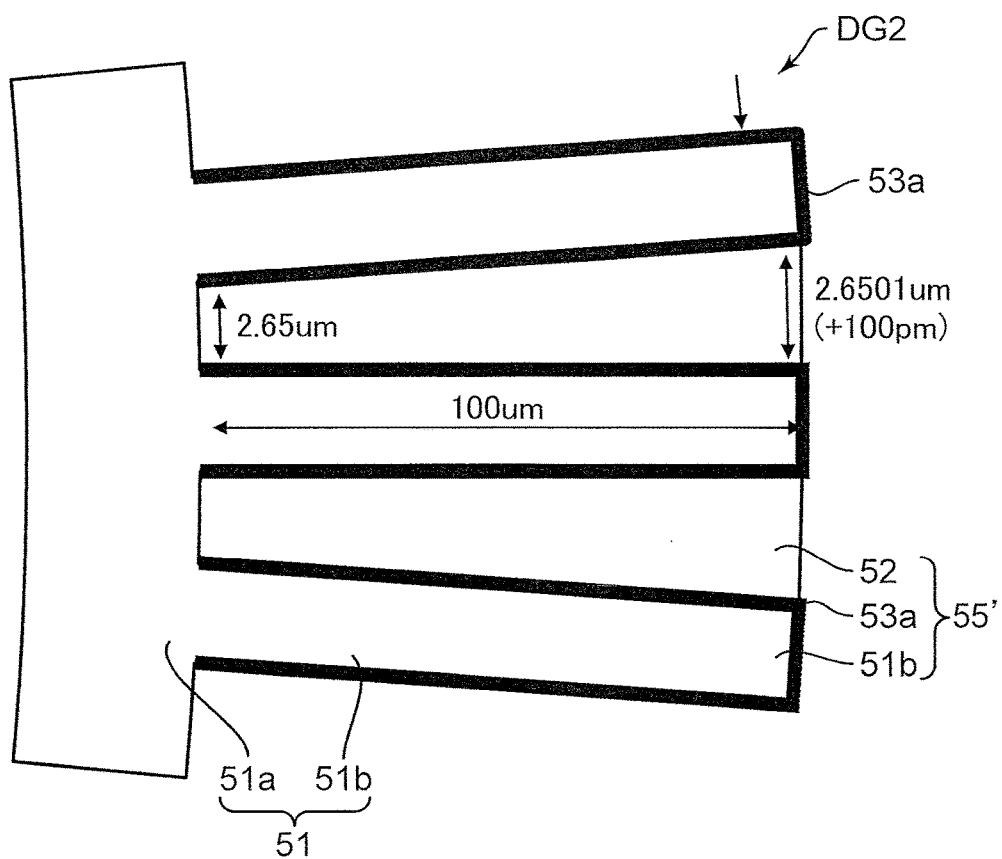

METAL GRATING FOR X-RAYS, PRODUCTION METHOD FOR METAL GRATING FOR X-RAYS, METAL GRATING UNIT FOR X-RAYS, AND X-RAY IMAGING DEVICE

RELATED APPLICATIONS

This is a U.S. National Phase Application under 35 USC 371 of International Application PCT/JP2014/069517 filed on Jul. 24, 2014.

This application claims the priority of Japanese application no. 2013-199968 filed September 26, the entire content of which is hereby incorporated by reference.

TECHNICAL FIELD

The present invention relates to an X-ray metal grating structure in which a plurality of structural portions mutually having the same shape are periodically arranged, and an X-ray metal grating structure production method for producing the X-ray metal grating structure. The present invention also relates to an X-ray metal grating unit constructed by arranging a plurality of the X-ray metal grating structures side-by-side, and an X-ray imaging device using the X-ray metal grating structure or the X-ray metal grating unit.

BACKGROUND ART

In the case of a one-dimensional structure, a diffraction grating is utilized in optical systems of various devices, as a spectral element having a periodic structure composed of a large number of parallel members, and, in recent years, its application to X-ray imaging devices has also been attempted. In terms of a diffraction process, the diffraction grating can be classified into a transmissive diffraction grating and a reflective diffraction grating, wherein the transmissive diffraction grating includes an amplitude-type diffraction grating (absorptive diffraction grating) in which a plurality of light-absorbing (absorptive) members are periodically arranged on a light-transmissive substrate, and a phase-type diffraction grating in which a plurality of optical phase-shifting members are periodically arranged on a light-transmissive substrate. As used herein, the term "absorption (absorptive)" means that light is absorbed by a diffraction grating at a rate of greater than 50%, and the term "transmission (transmissive)" means that light is transmitted through a diffraction grating at a rate of greater than 50%.

A diffraction grating for near infrared light, visible light, or ultraviolet light can be relatively easily produced, because near infrared light, visible light and ultraviolet light are sufficiently absorbed by a very thin metal. For example, an amplitude-type diffraction grating based on a metal grating structure is produced by vapor-depositing a metal on a substrate made of glass or the like to form a metal film on the substrate and patterning the metal film to form a grating structure. In an amplitude-type diffraction grating for visible light, when aluminum (Al) is used as the metal, it is enough for the metal film to have a thickness, for example, of about 100 nm, because a transmittance of aluminum with respect to visible light (about 400 nm to about 800 nm) is 0.001% or less.

On the other hand, as is well known, X-ray is very low in terms of absorption by a material, and is not so large in terms of phase shift, in general. Even in the case where a diffraction grating for X-ray is produced using gold (Au) as a relatively favorable material, a required thickness of gold is about several ten μm. As above, in an X-ray diffraction grating, when a periodic structure is formed by arranging a transmissive member and an absorptive member or phase-shifting member which are even in width, at a pitch of several μm to several ten μm, a ratio of thickness to width (aspect ratio=thickness/width) in the gold portion has a high value of 5 or more Silicon fabrication techniques are suitable for forming such a periodic structure having a high aspect ratio, and a production method for such a metal grating structure is disclosed, for example, in the following Patent Literatures 1 and 2. A metal grating structure production method disclosed in the Patent Literatures 1 and 2 include: a resist layer forming step of forming a resist layer on a principal surface of a silicon substrate; a patterning step of patterning the resist layer and removing the patterned portion of the resist layer; an etching step of etching a portion of the silicon substrate corresponding to the removed portion of the resist layer by dry etching to thereby form a recess having a given depth; an insulation layer forming step of forming an insulation layer on an inner surface of the recess of the silicon substrate; a removal step of removing a portion of the insulation layer formed on a bottom of the recess; and an electroforming step of applying voltage across the silicon substrate to perform an electroforming process to thereby fill the recess with a metal, wherein an anodic oxidation process or a thermal oxidation process is used in the insulation layer forming step.

Meanwhile, in the case where a silicon oxide film (silicon dioxide (quartz, $SiO_2$) film (layer)) is used as the above insulation film when an X-ray metal grating structure is produced by the metal grating structure production method disclosed in the Patent Literatures 1 and 2, a thermal expansion coefficient of silicon dioxide is about $0.7 \times 10^{-6}$/K, whereas a thermal expansion coefficient of silicon is about $2.6 \times 10^{-6}$/K. For this reason, when a silicon oxide film serving as the above insulation layer is formed on the silicon substrate at a high temperature by a thermal oxidization process, and subsequently the silicon substrate formed with the silicon oxide film is cooled to normal temperature, due to a difference in thermal expansion coefficient between silicon and silicon dioxide, a thermal stress is generated in an X-ray metal grating structure produced from the silicon substrate. Therefore, in a process of producing an X-ray metal grating structure from a silicon substrate (silicon wafer), this thermal stress causes a strain in the X-ray metal grating structure, and thereby flatness of the X-ray metal grating structure deteriorates compared to flatness of the silicon substrate (silicon wafer).

Further, in the metal grating structure production method disclosed in the Patent Literatures 1 and 2, the metal grows from the bottom of the recess by an electroforming process (bottom-up growth). The present inventor found a phenomenon that, during this growth, the metal grows in such a manner that a width of a top thereof (a region adjacent to an opening of the recess) becomes slightly larger than a width of a bottom thereof. Then, due to this slight difference in width between the bottom and the top of the metal, a stress (hereinafter referred to appropriately as "electroforming stress (plating stress)" is generated. This electroforming stress also causes a strain in the X-ray metal grating structure, and thereby the flatness of the X-ray metal grating structure deteriorates compared to the flatness of the silicon substrate (silicon wafer).

CITATION LIST

Patent Literature

Patent Literature 1: JP 2012-150219A
Patent Literature 2: WO 2012/086121A

SUMMARY OF INVENTION

The present invention has been made in view of the above circumstances, and an object of the present invention is to provide an X-ray metal grating structure having higher flatness (flatness accuracy) and an X-ray metal grating structure production method therefor. The present invention is also directed to providing an X-ray metal grating unit constructed by arranging a plurality of the X-ray metal grating structures side-by-side, and an X-ray imaging device using the X-ray metal grating structure or the X-ray metal grating unit.

The present invention provides an X-ray metal grating structure which has a grating region in which a plurality of structural portions are periodically provided, wherein an air gap is formed between each of the plurality of first structural portions and a second structural portion as a remaining part of the grating region other than the plurality of first structural portions. Thus, the X-ray metal grating structure of the present invention is formed as a grating structure having high flatness. A production method therefor includes a step of forming the air gap between the first structural portion and the second structural portion. Thus, the production method makes it possible to produce an X-ray metal grating structure having high flatness. The present invention further provides an X-ray metal grating unit and an X-ray imaging device each comprising the X-ray metal grating structure.

The above and other objects, features and advantages of the present invention will be apparent from the following detailed description and the accompanying drawings.

BRIEF DESCRIPTION OF DRAWINGS

FIG. 2 is a diagram illustrating a production method for the X-ray metal grating structure depicted in FIG. 1.

FIG. 5 is a perspective view depicting a silicon substrate in a production process of the X-ray metal grating structure depicted in FIG. 1.

FIG. 9 is a partial sectional view of an X-ray metal grating structure as a comparative example.

DESCRIPTION OF EMBODIMENTS

Based on the drawings, an embodiment of the present invention will now be described. It should be noted that elements or components assigned with the same reference sign in the figures means that they are the same elements or components, and duplicated descriptions thereof will be appropriately omitted. In this specification, for a generic term, a reference sign without any suffix is assigned thereto, and, for a term meaning an individual element or component, a reference sign with a suffix is assigned thereto.

First Embodiment; X-Ray Metal Grating Structure

Figure 1:
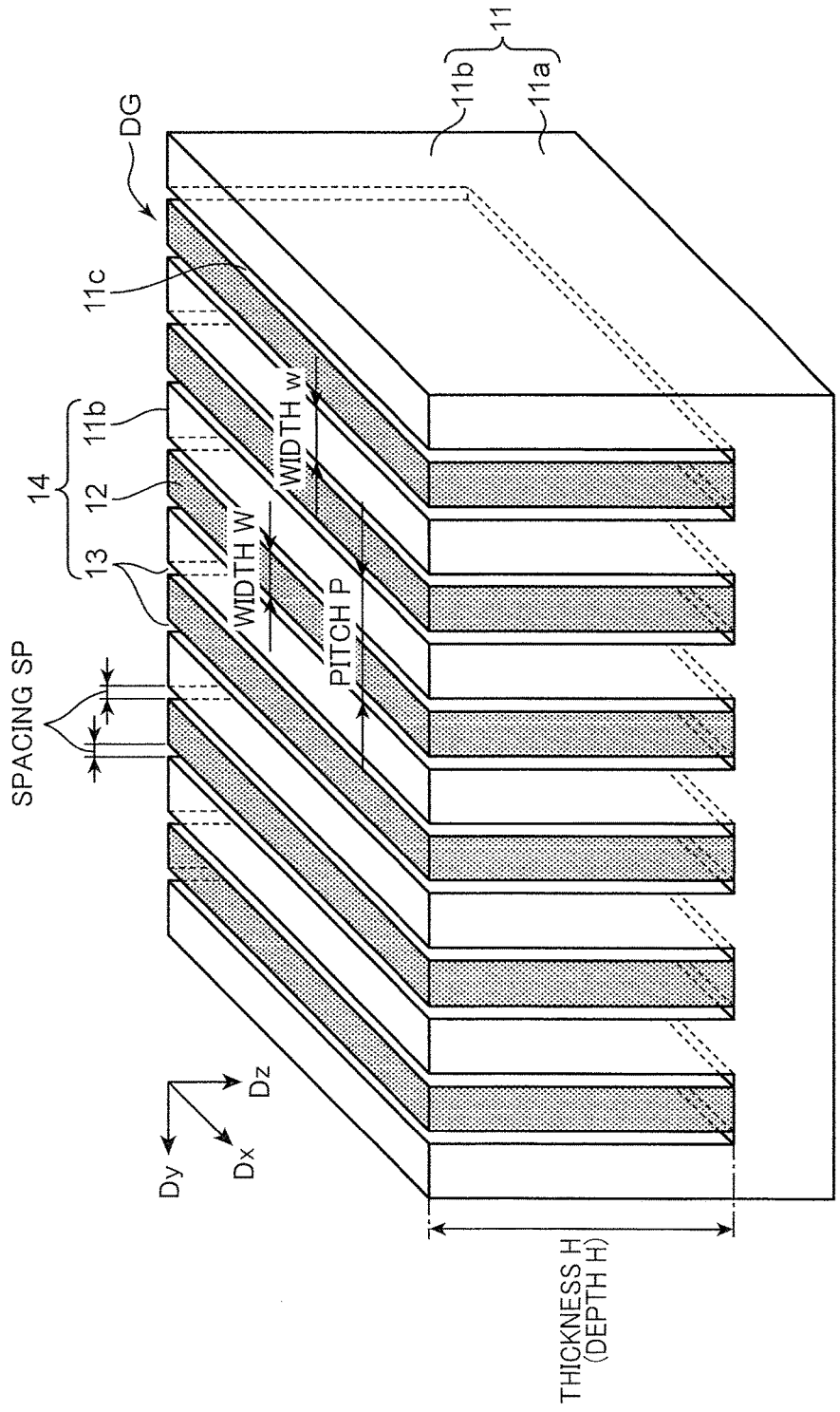
FIG. 1 is a perspective view depicting a configuration of an X-ray metal grating structure according to a first embodiment.

FIG. 1 is a perspective view depicting a configuration of an X-ray metal grating structure according to a first embodiment of the present invention. FIGS. 2 to 4 are diagrams illustrating a production method for the X-ray metal grating structure according to the first embodiment. FIG. 5 is a perspective view depicting a silicon substrate in a production process of the X-ray metal grating structure according to the first embodiment. FIG. 6 is a diagram illustrating another production method for the X-ray metal grating structure according to the first embodiment.

As depicted in FIG. 1, the X-ray metal grating structure DG according to this embodiment includes a grating-forming workpiece 11 having one surface formed with a grating region 14 in which a plurality of structural portions 11b mutually having the same shape are periodically provided. The grating region 14 includes: the plurality of structural portions 11b; a remaining portion 12 as a remaining part of the grating region 14 other than the plurality of structural portions 11b; and an air gap 13 formed between each of the structural portions 11b and the remaining portion 12, in such a manner as to provide a given spacing therebetween in a given planar (in-plane) direction on a grating plane of the grating region 14, and extend along a direction normal to the grating plane of the grating region 14 (along a direction orthogonal to the given planar (in-plane) direction). In this embodiment, the structural portion 11b is equivalent to one example of "first structural portion" set forth in the appended claims, and the remaining portion 12 is equivalent to one example of "second structural portion" set forth in the appended claims.

More specifically, in one aspect, in the case of a one-dimensional grating structure as in the embodiment depicted in FIG. 1, when an orthogonal coordinate system DxDyDz is set as depicted in FIG. 1, a grating region 14 is formed on a plate-or layer-shaped portion (base plate portion) 11a along a plane Dx-Dy of a grating-forming workpiece 11. This grating region 14 has: a plurality of structural portions 11b each having a given thickness H (a length in a direction Dz perpendicular to a grating plane Dx-Dy (a direction normal to the grating plane Dx-Dy); a depth H) and linearly extending in a direction Dx as a specific one of three mutually orthogonal directions; a plurality of remaining portions 12 each having the given thickness H and linearly extending in the direction Dx; and an air gap 13 formed between corresponding ones of the structural portions 11b and the remaining portions 12, in such a manner as to provide a given spacing SP therebetween in a given planar (in-plane) direction on the grating plane Dx-Dy of the grating region 14 (in the case of a one-dimensional grating structure as in the embodiment depicted in FIG. 1, in an aftermentioned direction Dy), and extend along the direction Dz normal to the grating plane Dx-Dy of the grating region 14, wherein the plurality of structural portions 11b and the plurality of remaining portions 12 are alternately arranged via the air gap 13 in a direction Dy orthogonal to the direction Dx, and in parallel to a plane Dx-Dz whose normal direction is coincident with the direction Dy. Thus, the plurality of structural portions 11b are arranged at given intervals in the direction Dy orthogonal to the direction Dx. In other words, the plurality of remaining portions 12 are arranged at given intervals in the direction Dy orthogonal to the direction Dx as the specific direction. In this embodiment, the above given interval (pitch) P is set to a constant value. That is, the plurality of structural portions 11b (plurality of remaining portions 12) are arranged at even intervals P in the direction Dy orthogonal to the direction Dx. In this embodiment, the structural portion 11b and the remaining portion 12 are made, respectively, of first and second grating region materials each having a respective one of mutually different first and second characteristic values of a given characteristic with respect to X-ray, wherein at least one of the first and second grating region materials is a metal.

In another aspect, in the case of a one-dimensional grating structure as in the embodiment depicted in FIG. 1, by providing, in the grating-forming workpiece 11, a plurality of recesses 11c each having the given thickness H (depth H) and linearly extending in the direction Dx as the specific direction, the plurality of structural portions 11b each having a given thickness H and linearly extending in the direction Dx are formed to extend from the base plate portion 11a of the grating-forming workpiece 11 and stand vertically (in a direction −Dz) from the base plate portion 11a of the grating-forming workpiece 11. Therefore, each of the plurality of recesses 11c is a plate-or layer-shaped space along the plane Dx-Dz orthogonal to the plane Dx-Dy, and each of the plurality of structural portions 11b is a plate-or layer-shaped member along the plane Dx-Dz perpendicular to the plane Dx-Dy. Thus, the plurality of recesses 11c and the plurality of structural portions 11b are alternately arranged in the direction Dy orthogonal to the direction Dx, and in parallel to the plane Dx-Dz whose normal direction is coincident with the direction Dy. The plurality of structural portions 11b are arranged at given intervals in the direction Dy orthogonal to the direction Dx. In other words, the plurality of recesses 11c are arranged at given intervals in the direction Dy orthogonal to the direction Dx. In this embodiment, the above given interval (pitch) P is set to a constant value. That is, the plurality of structural portions 11b (plurality of recesses 11c) are arranged at even intervals P in the direction Dy orthogonal to the direction Dx. Then, in this embodiment, each of the plurality of remaining portions 12 is provided within a respective one of the plurality of recesses 11c, with a given spacing SP with respect to a corresponding one of the plurality of structural portions 11b, wherein the structural portion 11b is formed of a first grating region material, i.e., a material of the grating-forming workpiece 11, having a first value of a given characteristic with respect to X-ray, and the remaining portion 12 is formed of a second grating region material having a second value different from the first value. In this way, an air gap 13 is formed between corresponding ones of the structural portions 11b and the remaining portions 12, in such a manner as to provide a given spacing SP therebetween in a given planar (in-plane) direction on the grating plane Dx-Dy of the grating region 14 (in the case of a one-dimensional grating structure as in the embodiment depicted in FIG. 1, in the direction Dy), and extend along the direction Dz normal to the grating plane Dx-Dy of the grating region 14. This air gap 13 is a plate-or layer-shaped space along the plane Dx-Dz orthogonal to the plane Dx-Dy. In one example, such a grating region 14 is formed by providing the recesses (concave portions) 11 in the flat plate-shaped grating-forming workpiece 11 to form the plurality of structural portions 11b, and forming each of the remaining portions 12 in a respective one of the recesses 11c with the gap 13 therebetween so as to avoid a contact with a corresponding one of the structural portions 11b. Further, at least one of the first and second grating region materials is a metal. In the above description, for the sake of simplicity of explanation, a plurality of portions each extending from the base plate portion 11a are described as the plurality of structural portions 11b, and a plurality of portions each provided within a respective one of the recesses 11c are described as the plurality of remaining portions 12. Alternatively, a plurality of portions each extending from the base plate portion 11a may be referred to as "plurality of remaining portions 12", and a plurality of portions each provided within a respective one of the recesses 11c may be referred to as "plurality of structural portions 11b".

In one example, the given characteristic with respect to X-ray is an X-ray transmittance (X-ray absorptance). In this case, a group of the plurality of structural portions 11b and a group of the plurality of remaining portions 12 function to transmit (or absorb) X-rays at different transmittances (or absorptances). Thus, in one embodiment, the thickness H of each of structural portions 11b, the thickness H of each of the plurality of remaining portions 12 and the given interval (pitch) P are appropriately set depending on a wavelength of X-rays to satisfy X-ray diffraction conditions to thereby allow the X-ray metal grating structure DG to function as an amplitude-type diffraction grating.

In another example, the given characteristic with respect to X-ray is an X-ray phase shift rate. In this case, respective groups of the plurality of structural portions 11b and the plurality of remaining portions 12 function to act to X-rays at different phase shift rates. Thus, in one embodiment, the thickness H of each of structural portions 11b, the thickness H of each of the plurality of remaining portions 12 and the given interval (pitch) P are appropriately set depending on a wavelength of X-rays to satisfy X-ray diffraction conditions to thereby allow the X-ray metal grating structure DG to function as a phase-type diffraction grating.

While the first grating region material of the structural portions 11b (the material of the grating-forming workpiece 11) may be arbitrary, it is preferably a type having a relatively small value of the given characteristic with respect to X-ray. Examples of the first grating region material include silicon, glass, resin, and a metal (including alloy) of an element having a relatively small atomic weight (relatively light element). From a viewpoint of being capable of forming a high-aspect ratio recess $11c$ at relatively high dimensional accuracy and in a relatively easy manner, the first grating region material is preferably silicon. The thermal expansion coefficient of silicon is $2.6 \times 10^{-6}/°$ C.

While the second grating region material of the remaining portions 12 may be arbitrary, it is preferably a type having a relatively large value of the given characteristic with respect to X-ray, from a viewpoint of being capable of reducing the thickness H of each of the remaining portions 12, i.e., the depth H of each of the remaining portions 12, so as to reduce the aspect ratio. For example, the second grating region material preferably contains a metal of an element having a relatively large atomic weight (relatively heavy element), specifically, at least one selected from the group consisting of gold (Au), platinum (Pt), iridium (Ir) and rhodium (Rh). Gold (Au) is an element having an atomic number of 79, and the thermal expansion coefficient thereof is $14.2 \times 10^{-6}/°$ C. Platinum (Pt) is an element having an atomic number of 78, and the thermal expansion coefficient thereof is $8.8 \times 10^{-6}/°$ C. Iridium (Ir) is an element having an atomic number of 77, and the thermal expansion coefficient thereof is $6.4 \times 10^{-6}/°$ C. Rhodium (Rh) is an element having an atomic number of 45, and the thermal expansion coefficient thereof is $8.2 \times 10^{-6}/°$ C. By forming the remaining portions 12 using such a material, the remaining portions 12 can relatively largely act to X-rays, so that it becomes possible to reduce the depth of each of the remaining portions to thereby more facilitate the production of the X-ray metal grating structure DG.

The aspect ratio means a ratio of the thickness H (depth H) to a width W of each of the remaining portions 12 (or each of the recesses $11c$) (in FIG. 1, it denotes a width of each of the remaining portions 12) (the aspect ratio=thickness H/width W). In the X-ray metal grating structure DG, each of the remaining portions 12 is formed with a high aspect ratio, for example, of 5 or more. Assuming that a width of each of the structural portions $11b$ is w, the pitch in FIG. 1 is expressed as follows: $P=w+W+2\times SP$. The width W of the remaining portion 12 is a length of the remaining portion 12 in the direction (width direction) Dy orthogonal to the direction Dx as the specific direction (longitudinal direction), and the thickness of the remaining portion 12 is a length of the remaining portion 12 in the direction (depth direction) Dz normal to the plane defined by the direction Dx and the direction Dy orthogonal to the direction Dx. The width w of the structural portion $11b$ is a length of the structural portion $11b$ in the direction (width direction) Dy orthogonal to the direction Dx as the specific direction (longitudinal direction).

The above X-ray metal grating structure DG has the air gap 13 formed between corresponding ones of the structural portions $11b$ and the remaining portions 12, so that a stress generated in the X-ray metal grating structure DG can be absorbed by the air gaps 13. Thus, this X-ray metal grating structure DG is formed as a grating structure having high flatness (flatness accuracy).

The X-ray metal grating structure DG having the above high-aspect ratio remaining portions 12 is produced by an X-ray metal grating structure production method which includes: a grating forming step of forming, on one surface of a grating-forming workpiece made of an electrically-conductive material, a grating region in which a plurality of structural portions mutually having the same shape are periodically provided via a recess; on-non-bottom-surface insulation layer forming step of forming an insulation layer on a surface of the recess in the grating-forming workpiece, except for a bottom surface of the recess; an electroforming step of applying voltage across the grating-forming workpiece to perform an electroforming process to thereby fill the recess with a metal; and an intervening-insulation layer removing step of removing the insulation layer formed on the surface of the recess in the on-non-bottom-surface insulation layer forming step, at least in a region intervening between the grating-forming workpiece and the metal filled in the electroforming step. The aforementioned recesses $11c$ may be composed, for example, of a plurality of periodically-arranged slit grooves, in the case of a one-dimensional grating structure, or may be composed, for example, of a plurality of periodically-arranged pillar-shaped holes (pillar-shaped openings) in the case of a two-dimensional grating structure. Further, in the case of a two-dimensional grating structure, when the grating-forming workpiece 11 is etched such that a plurality of periodically-arranged pillar-shaped portions are left as the plurality of structural portions $11b$, the recesses $11c$ may also be composed of the etched portions. In this case, the recesses may be formed as the structural portions, or a remaining part other than the recesses may serve as the structural portions. In the example illustrated in FIG. 1, the remaining part formed by the recesses $11c$ serves as the structural portions.

More specifically, in order to produce the X-ray metal grating structure according to this embodiment, first of all, a flat plate-shaped grating-forming workpiece 11 made of a given electrically-conductive material is preliminarily prepared (FIG. 2A). In this embodiment, a silicon substrate 30 is preliminarily prepared as one example of the grating-forming workpiece 11. The use of the silicon substrate 30 made of silicon as the grating-forming workpiece 11 makes it possible to utilize so-called "silicon fabrication techniques" in which microfabrication techniques have been almost established, so as to produce a microstructural grating region 14 with a relatively high degree of accuracy, and form a plurality of high-aspect ratio slit grooves SD, as one example of the recesses $11c$. Preferably, the silicon substrate 30 is n-type silicon in which most carriers are electrons. The n-type silicon has abundant conduction electrons. Thus, when the silicon is connected to a negative electrode, and a negative potential is applied thereto to cause polarization at a cathode, a so-called "ohmic contact" is established with respect to a plating solution 47 in an aftermentioned electroforming step, and a resulting current flow is likely to cause a reduction reaction, resulting in an increase in metal precipitation.

Then, a plurality of slit grooves SD is formed as the recesses $11c$ to thereby form, in one principal surface of the silicon substrate 30, a grating region 14 in which a plurality of structural portions $11b$ mutually having the same shape are periodically provided (grating forming step; FIG. 2B to FIG. 3B).

Figure 3A:
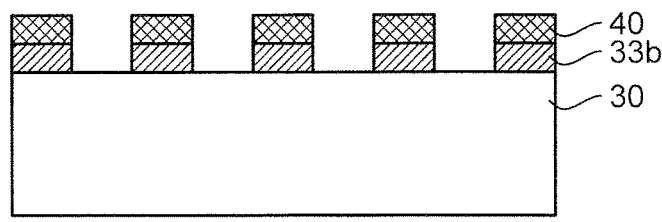
FIG. 3 is a diagram illustrating steps subsequent to those in FIG. 2, in the production method for the X-ray metal grating structure depicted in FIG. 1.

In one example of the grating forming step, first of all, a resist layer $33a$ is formed on the principal surface of the silicon substrate 30 (resist layer forming sub-step). Then, this resist layer 33 is patterned, and the patterned portion thereof is removed (patterning sub-step; FIGS. 2C, 2D and 3A). The resist layer means a layer functioning as a protective film against etching during the etching.

For example, the resist layer $33a$ may be composed of a silicon oxide film (a silicon dioxide film, a quartz film or a $SiO_2$ film) having an insulating property and resistance to a subsequent etching process for the silicon substrate 30. This silicon oxide film $33a$ is used as the resist layer $33a$ to be patterned, and a photosensitive resin layer (photoresist film) 40 is used to pattern the silicon oxide film 33a. The term "having resistance" does not mean that an influence of etching is fully eliminated during an etching process, but means that the influence of etching is relatively lowed. This means that during a period of etching a target portion, it is possible to serve as a protective film capable of protecting a non-target portion which should not be etched.

More specifically, the silicon oxide film 33a is formed as the resist layer 33a on a surface of the silicon substrate 30. The silicon oxide film 33a is formed by any one of heretofore-known commonplace means, such as a thermal oxidation process, a chemical vapor deposition process, an anodic oxidation processor, and other deposition process (other vapor deposition process or a sputtering process). As one example, in the thermal oxidation process, an oxygen atmosphere (which may contain inert gas) or water vapor is introduced into a quartz tube in which the silicon substrate 30 is disposed, and the quartz tube is heated by a heater, so as to heat the silicon substrate 30 to a high temperature in the oxygen atmosphere or in a gaseous atmosphere of the water vapor, so that a silicon oxide film 33a having a given thickness is formed on the surface of the silicon substrate 30. As another example, in the chemical vapor deposition (CVD) process, tetraethoxysilane (TEOS) as one type of organic silane is heated and bubbled by carrier gas to form TEOS gas, and then oxidation gas such as oxygen or ozone, and dilution gas such as helium, are mixed with the TEOS gas, to form raw material gas. Then, the raw material gas is introduced into a CVD apparatus such as a plasma CVD apparatus or a normal-temperature ozone CVD apparatus, and a silicon oxide film 33a having a given thickness is formed on a surface of the silicon substrate 30 inside the CVD apparatus. As yet another example, in the anodic oxidization process, a positive electrode of a power supply is connected to the silicon substrate 30, and a cathode electrode connected to the negative electrode of the power supply and the silicon substrate 30 are immersed in an electrolyte solution. Then, upon supplying current, a silicon oxide film 33a having a given thickness is formed on a surface of the silicon substrate 30. The silicon oxide film 33a is formed at least on an upper surface of the silicon substrate 30. Alternatively, it may also be formed on a back surface and/or a side surface thereof. The use of the silicon oxide film 33a as the resist layer 33a makes it possible to use any one of the heretofore-known commonplace means such as the thermal oxidation process, the chemical vapor deposition process and the anodic oxidation process, and thus relatively easily form the silicon oxide film 33a.

Subsequently, a photosensitive resin layer 40 is formed on the silicon oxide film 33a formed on the silicon substrate 30, for example, by spin coating (FIG. 2B). The photosensitive resin layer 40 used here is a material which is usable in lithography and whose physical properties such as solubility are changed by light (including not only visible light but also ultraviolet light), an electron beam or the like. However, the present invention is not limited thereto. For example, in place of the photosensitive resin layer 40, a resist layer for electron beam exposure may be used. Subsequently, as a photolithography sub-step, the photosensitive resin layer 40 is patterned by a lithography process (FIG. 2C), and the patterned portion thereof is removed (FIG. 2D). More specifically, a lithography mask 41 is put on the photosensitive resin layer 40, and ultraviolet light 42 is radiated onto the photosensitive resin layer 40 through the lithography mask 41, so that the photosensitive resin layer 40 is subjected to pattern exposure and development (FIG. 2D). Then, an unexposed portion (or exposed portion) of the photosensitive resin layer 40 is removed (FIG. 2D).

Figure 3B:
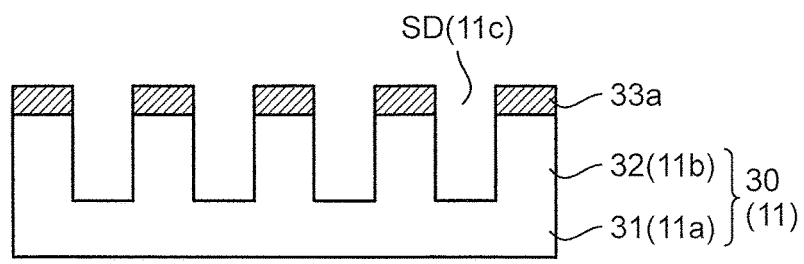

Subsequently, the silicon oxide film 33a is patterned in such a manner that a portion of the silicon oxide film 33a corresponding to a portion of the photosensitive resin layer 40 removed by etching is removed using the patterned photosensitive resin layer 40 as a mask (FIG. 3B). More specifically, the silicon oxide film 33a is patterned, for example, by reactive etching (RIE) using $CHF_3$ gas. Alternatively, the silicon oxide film 33a may be patterned, for instance, by wet etching using hydrofluoric acid. The etching of the silicon oxide film 33a as the resist layer 33a in the patterning sub-step may be performed by any other etching process.

As above, this embodiment, the resist layer (first resist layer) 33a serving as a first pattern mask for etching the silicon substrate 30 is formed, and further the photosensitive resin layer (second resist layer) 40 serving as a second pattern mask for etching the resist layer 33a is formed. Then, in order from the side of the surface, the photosensitive resin layer 40 is patterned using the lithography mask 41, and the resist layer 33a is patterned using the patterned photosensitive resin layer 40 as a mask.

Then, a portion of the silicon substrate 30 corresponding to portions of the photosensitive resin layer 40 and the resist layer 33a removed by dry etching is etched in the direction Dz, i.e., the normal direction to reach a given depth H. In this manner, the slit grooves SD (one example of the recesses 11c) is formed (FIG. 3B; etching sub-step). FIG. 5 depicts one example of a structure of the silicon substrate 30 after the etching sub-step. In this connection, FIG. 3B depicts a section of the silicon substrate 30 taken along the line I-I in FIG. 5.

More specifically, the silicon substrate 30 is etched by ICP (Inductively Coupled Plasma) dry etching to the given depth H from the surface of the silicon substrate 30, using the patterned photosensitive resin layer 40 and resist layer 33a as a mask. Through this ICP dry etching, the photosensitive resin layer 40 is removed. Further, the resist layer 33a may also be slightly etched.

The ICP dry etching is capable of performing vertical etching with a high aspect ratio. Thus, it is preferably an ASE process using an ICP apparatus. The ASE (Advanced Silicon Etch) process is configured to repeatedly perform a step of etching a silicon substrate by RIE (reactive ion etching) using F radicals and F ions in $SF_6$ plasma, and a step of depositing a polymer film having a composition close to Teflon (trademark) on a wall surface through a polymerization reaction of $CF_X$ radicals and ions thereof in $C_4F_8$ plasma to act as a protective film. Further, in view of the capability of performing vertical etching with a high aspect ratio, it is more preferable to alternately perform a side wall protection and a bottom surface etching by alternately repeating a $SF_6$ plasma rich state and a $C_4F_8$ plasma rich state, as in a Bosch process. The dry etching process is not limited to the ICP dry etching, but may be any other technique. For example, an etching technique may be parallel plate type reactive ion etching (RIE), magnetic neutral line plasma (NLD) dry etching, chemically assisted ion beam (CAIB) etching, or electron cyclotron resonance reactive ion beam (ECRIB) etching.

A plate-shaped portion (layer-shaped portion or wall portion) 32 of the silicon substrate 30 remaining along the plane Dx-Dz after the etching is formed as the plurality of structural portions 11b, and a plate-shaped portion (base portion) 31 of the silicon substrate 30 remaining along the plane Dx-Dy after the etching is formed as the base plate portion 11a.

Figure 3C:
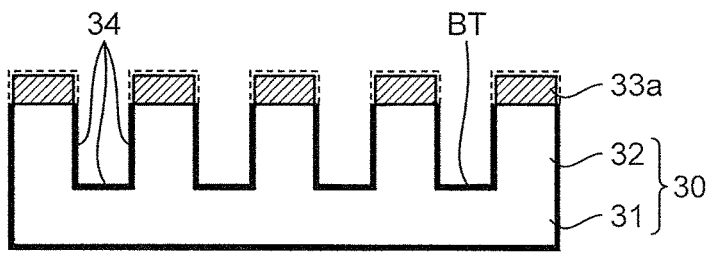
Figure 3D:
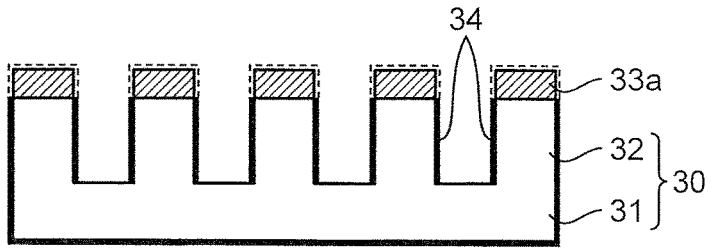

Then, an insulation layer is formed at least on surfaces of the slit grooves SD (recesses 11c) of the silicon substrate 30 (grating-forming workpiece 11), except for bottom surfaces of the slit grooves SD (on-non-bottom-surface insulation layer forming step); FIGS. 3C and 3D).

More specifically, first of all, an insulation layer 34 having a thickness is formed at least over the entire inner surface of each of the slit grooves SD of the silicon substrate 30 to have an insulating property against an electroforming process in the aftermentioned electroforming step (FIG. 3C, insulation layer forming sub-step). This insulation layer 34 may be formed by any heretofore-known commonplace means such as a deposition process, a sputtering process or the like for forming a film of a given insulation material. In this embodiment, the silicon substrate 30 is used, and therefore the insulation layer 34 is a silicon oxide film 34. For example, this silicon oxide film is formed using the aforementioned thermal oxidation process or anodic oxidation process. In the case of forming the insulation layer 34 using the thermal oxidation process, it is possible to form a silicon oxide film 34 which is dense and excellent in adhesion, and relatively easily control a film thickness thereof. In the case of forming the insulation layer 34 using the anodic oxidation process, it is possible to form a silicon oxide film 34 which is dense and excellent in adhesion and film thickness uniformity, and relatively easily control a film thickness thereof. Thus, this production method for the X-ray metal grating structure DG can form an insulation layer 34 capable of being densified with a given thickness, while ensuring electrical insulation against an electroforming process in the electroforming step. In this regard, in the case where the resist layer 33a is a silicon oxide film 33a, almost no oxide film is formed on the resist layer 33a by an influence of the anodic oxidation during the insulation layer forming sub-step. On the other hand, in the case where the insulation layer forming sub-step is performed by a deposition process even when the resist layer 33a is a silicon oxide film 33a, a silicon oxide film 34 is formed on the resist layer 33a, as indicated by the broken line in FIG. 3C.

Then, a portion of the insulation layer 34 formed on a bottom BT of each of the slit grooves SD is removed (removal sub-step; FIG. 3). More specifically, the portion of the insulation layer 34 formed on the bottom BT of each of the slit grooves SD is removed, for example, by ICP dry etching using $CHF_3$ gas.

In this sub-step, the ICP dry etching has high vertical directionality, so that at a time when the portion of the insulation layer 34 formed on the bottom portion BT of each of the slit grooves SD is removed, a portion of the insulating layer 34 formed on inner side surfaces of the slit groove SD (a portion of the insulating layer 34 formed on opposite wall surfaces (opposite side surfaces) of each of a plurality of plate-shaped portions 32 of the silicon substrate 30) is left in a state in which it has a sufficient thickness capable of functioning as an insulation layer. The remaining insulating layer 34 formed on the inner side surfaces of the slit groove SD may have a thickness, e.g., a thickness of about 10 nm or more, which is enough to fulfill a function of blocking a voltage to be applied to the plate-shaped portion 32 of the silicon substrate 30 (a function of electrically insulating the plate-shaped portion 32) in the subsequent electroforming step, in cooperation with the resist layer (silicon oxide film) 33a having an insulating property.

Figure 4A:
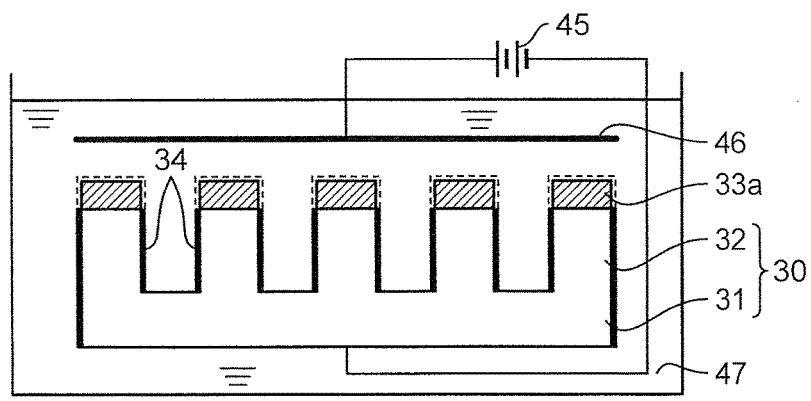
FIG. 4 is a diagram illustrating steps subsequent to those in FIG. 3, in the production method for the X-ray metal grating structure depicted in FIG. 1.

Then, voltage is applied across the silicon substrate 30 (grating-forming workpiece 11) to perform an electroforming process (electroplating process) to thereby fill each of the slit grooves SD (recesses 11c) with a metal (electroforming step; FIG. 4A). More specifically, a negative electrode of a power supply 45 is connected to the silicon substrate 30, and an anode electrode 46 connected to a positive electrode of the power supply 45 and the silicon substrate 30 are immersed in a plating solution 47. In the case where a silicon oxide film is formed on a portion of the silicon substrate 30 to which the negative electrode of the power supply 45 is connected, the portion is removed in order to achieve conduction between the power supply 45 and the silicon substrate 30. For example, in the case where the silicon oxide film 34 is formed on a surface of the base plate portion 11a of the silicon substrate 30 through the on-non-bottom-surface insulation layer forming step, the silicon oxide film 34 formed on the surface of the base plate portion 11a of the silicon substrate 30 is removed, for example, by dry etching, so as to achieve electrical connection between the power supply 45 and the silicon substrate 30. After that, the negative electrode of the power supply 45 is connected to the surface of the base plate portion 11a of the silicon substrate 30. Thus, through electroforming, a metal precipitates and grows from the side of the silicon substrate 30 (plate-shaped portion 31) at the bottoms of the slit grooves SD.

Figure 4B:
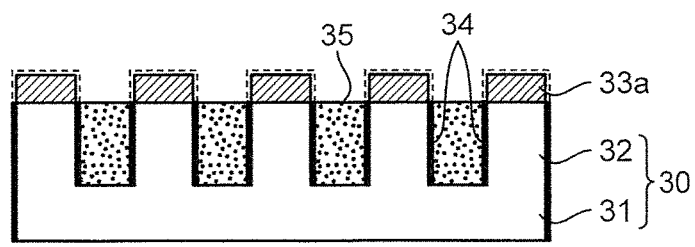

Then, when the slit grooves SD are filled with the metal, the electroforming is terminated (FIG. 4B). In this way, metal 35 grows by the same thickness H as that of the plate-shaped portions 32 of the silicon substrate 30. In this way, the metal 35 is filled in the slit grooves SD, and the remaining portions 12 made of the metal 35 is formed. Preferably, the metal 35 is at least one selected from the group consisting of gold (Au), platinum (Pt), iridium (Ir) and rhodium (Rh), which are preferred examples of a metal having a relatively large atomic weight. These metals relatively largely act to X-rays, so that it becomes possible to reduce the depth H of each of the recesses 11c. Therefore, the above production method for the X-ray metal grating structure DG can easily produce a grating structure.

Figure 4C:
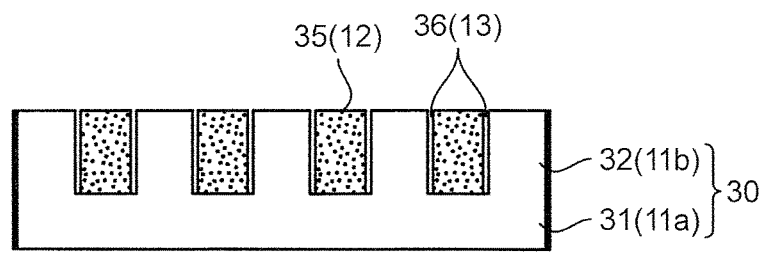

Then, the insulation layer 34 formed on the inner surface of each of the slit grooves SD (recesses 11c) formed in the on-non-bottom-surface insulation layer forming step is removed at least in a region intervening between corresponding ones of the plate-shaped portions 32 of the silicon substrate 30 (structural portions 11b of the grating-forming workpiece 11) and the metal portions 35 (remaining portions 12) filled in the electroforming step (intervening-insulation layer removing step; FIG. 4C). More specifically, the silicon substrate 30 (grating-forming workpiece 11) after being subjected to the electroforming step is immersed in a hydrofluoric acid solution capable of solving the silicon oxide film 34. As a result, a portion of the insulation layer 34 intervening between corresponding ones of the plate-shaped portions 32 of the silicon substrate 30 and the metal portions 35 is removed, so that an air gap 36 serving as the air gap 13 is formed between corresponding ones of the plate-shaped portions 32 of the silicon substrate 30 and the metal portions 35 filled in the electroforming step, in such a manner as to provide a given first spacing therebetween in a given planar (in-plane) direction on a grating plane Dx-Dy of the grating region 14 (in a one-dimensional grating structure as in the embodiment depicted in FIG. 1, in the direction Dy), and extend along the direction Dz normal to the grating plane Dx-Dy of the grating region 14. Further, the silicon oxide film 33a of the resist later 33a formed on tops of the plate-shaped portions 32 of the silicon substrate 30 is also removed.

Figure 6A:
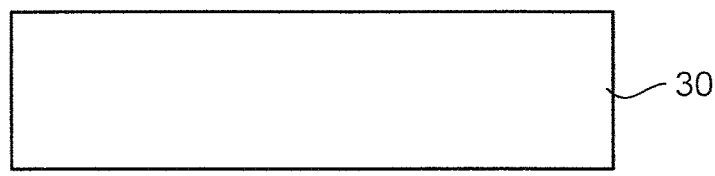
FIG. 6 is a diagram illustrating another production method for the X-ray metal grating structure depicted in FIG. 1.
Figure 6B:
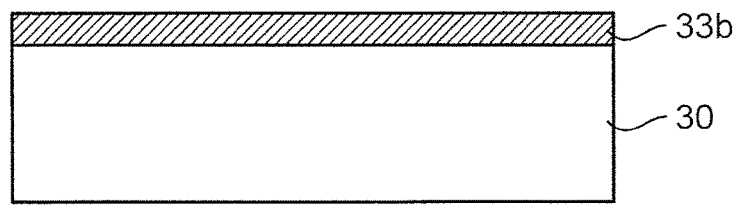
Figure 6C:
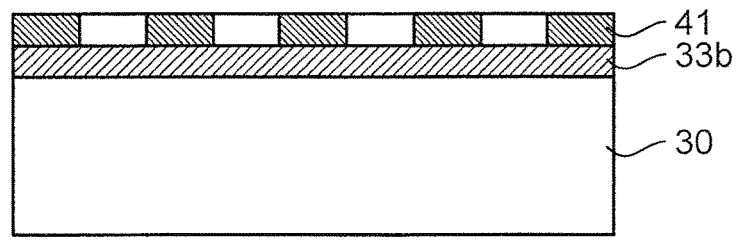
Figure 6D:
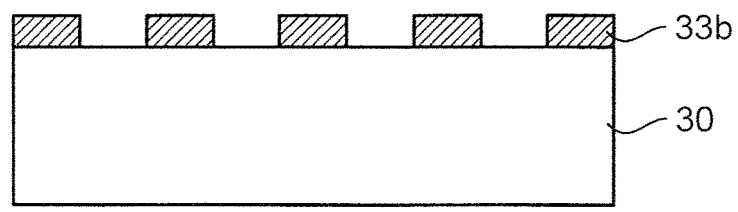

In the grating forming step in the above production process, the silicon oxide film 33a is used as the resist layer. Alternatively, a photosensitive resin layer 33b may be used as the resist layer. More specifically, as depicted in FIG. 6A, a flat plate-shaped grating-forming workpiece 11 made of a given electrically-conductive material is preliminarily prepared, as with FIG. 2A. Then, a photosensitive resin layer 33b, e.g., an ultraviolet curable type, is formed as a resist layer 33b on one principal surface of the silicon substrate 30, for example, by spin coating (resist layer forming sub-step; FIG. 6B). Then, a lithography mask 41 is put on the resist layer 33b, and ultraviolet light 42 is radiated onto the resist layer 33b through the lithography mask 41, so that the resist layer 33b is subjected to pattern exposure and development. Then, an unexposed portion (or exposed portion) of the resist layer 33b is removed (patterning sub-step; FIGS. 6B and 6C). Then, by using the patterned resist layer 33b as a mask, a portion of the silicon substrate 30 corresponding to a portion of the resist layer 33b removed by etching is etched to a given depth H in the Dz direction. By this grating-forming step, the plurality of slit grooves SD may be formed as the recesses 11c to thereby form, on the one principal surface of the silicon substrate, the grating region 14 in which the plurality of structural portions 11b mutually having the same shape are periodically provided.

Through the aforementioned production steps, the X-ray metal grating structure DG having the configuration depicted in FIG. 1 is produced. In the production method for the X-ray metal grating structure DG, the air gap 13 (in the above embodiment, the air gap 36) is formed between corresponding ones of the structural portions 11b (in the above embodiment, the plate-shaped portions 32 of the silicon substrate 30) and the remaining portions 12 (in the above embodiment, the metal portions 35), so that it becomes possible to absorb a stress generated in X-ray metal grating structure DG after production, by the air gaps 13. Therefore, the production method for the X-ray metal grating structure DG makes it possible to produce the X-ray metal grating structure DG with higher flatness (flatness accuracy).

Based on the formation of the air gaps 13, the production method for the X-ray metal grating structure DG has the following advantages.

A first advantage is that the X-ray metal grating structure DG becomes more bendable. The plurality of air gaps 13 formed in the grating region 14 act in the same manner as a cut form in a plate, so that the X-ray metal grating structure DG becomes more bendable. In a different viewpoint, due to the plurality of air gaps 13 formed in the grating region 14, an effective thickness of the X-ray metal grating structure DG is substantially equal to a thickness of the base plate portion 11a, i.e., becomes smaller, so that the X-ray metal grating structure DG becomes more bendable. For example, in the case where the X-ray metal grating structure DG is applied to an X-ray imaging device, an X-ray source of the X-ray imaging device radiates X-rays in a radial pattern as in a point light source. Thus, if the X-ray metal grating structure DG has a flat plate shape, due to a high aspect ratio thereof, X-rays obliquely enters the grating plane in the vicinity of an end of the X-ray metal grating structure DG, an entirety or part of X-ray which should be transmitted through the structural portions 11 are absorbed by the remitting portions 12, i.e., the metals, thereby leading to the occurrence of so-called "vignetting". In this regard, the bendable X-ray metal grating structure DG is suitable for X-ray imaging devices. When the X-ray metal grating structure DG is bent, it is easy to bend it such that the grating plane is bulged outwardly. However, it may be bent such that the grating plane is depressed inwardly. Even in this case, it is possible to sufficiently realize a curvature necessary for a second diffraction grating in an aftermentioned Talbot interferometer, e.g., a curvature radius of about 1 m.

A second advantage is that it is possible to prevent deformation of the X-ray metal grating structure DG due to environmental temperature. As mentioned above, the thermal expansion coefficient of silicon is about $2.6 \times 10^{-6}/°$ C., and the thermal expansion coefficient of gold is about $14.2 \times 10^{-6}/°$ C. Thus, in the case where the structural portions 11b and the remaining portions 12 in the X-ray metal grating structure DG are formed, respectively, of silicon and gold, and the environmental temperature around the X-ray metal grating structure DG changes, for example, by 100° C., expansion in a bottom end of each of the remaining portions 12 depends on expansion of the base plate portion 11a, i.e., primarily depends on expansion of silicon. Specifically, a width of the bottom end of the remaining portion 12 expands as follows: $2.65 + 2.65 \times 2.6 \times 10^{-6} \times 100 = 2.651$ μm. On the other hand, expansion in a top end of the remaining portion 12 primarily depends on expansion of gold. Specifically, a width of the top end of the remaining portion 12 expands as follows: $2.65 + 2.65 \times 14.2 \times 10^{-6} \times 100 = 2.654$ μm. Thus, a dimensional difference in the width direction (direction Dy) between the bottom and top ends of the remaining portion is calculated as follows: $2.654 - 2.651 = 0.003$ μm (3 nm). Therefore, in a structure where the structural portion 11b and the remaining portion 12 are in contact with each other without the air gap 13 in the X-ray metal grating structure DG according to this embodiment, due to the relatively large expansion in the top end of the remaining portion 12, a stress is generated to cause undesirable deformation, like warping, in the X-ray metal grating structure DG. This deformation deteriorates stability in flatness or shape of the X-ray metal grating structure DG, against a change in environmental temperature. Moreover, in a situation where the X-ray metal grating structure DG is fixed by a jig, the deformation is likely to lead to breakage of the X-ray metal grating structure DG. In the X-ray metal grating structure DG according to this embodiment, the air gap 13 is provided between corresponding ones of the structural portions 11b and the remaining portions 12, so that it becomes possible to absorb the relatively large expansion in the top end of each of the remaining portions 12 to thereby prevent the undesirable deformation of the X-ray metal grating structure DG due to a change in environmental temperature.

In the above production method for the X-ray metal grating structure DG, the grating-forming workpiece 11 (in the above embodiment, the silicon substrate 30) is etched by dry etching using a Bosch process, so that it becomes possible to more flatly form side surfaces of each of the recesses 11c (in the above embodiment, the side surfaces of each of the plate-shaped portions 32 of the silicon substrate 30) and thus form the X-ray metal grating structure DG with a high degree of accuracy.

In the above production method for the X-ray metal grating structure DG, with a view to approximately uniforming growth lengths of the metals 45 which are caused to grow in the slit grooves SD by the electroforming process, it is possible to add a surface area-increasing step of further etching a portion of the silicon substrate corresponding to the bottom of each of the recesses exposed by removing, in the removal sub-step, the portion of the insulation layer formed at the bottom of the recess, to thereby increase a surface area of the bottom of the recess, as compared to the surface area before the etching.

Next, an inventive example and a comparative example will be described.

Inventive Example and Comparative Example

Figure 7:
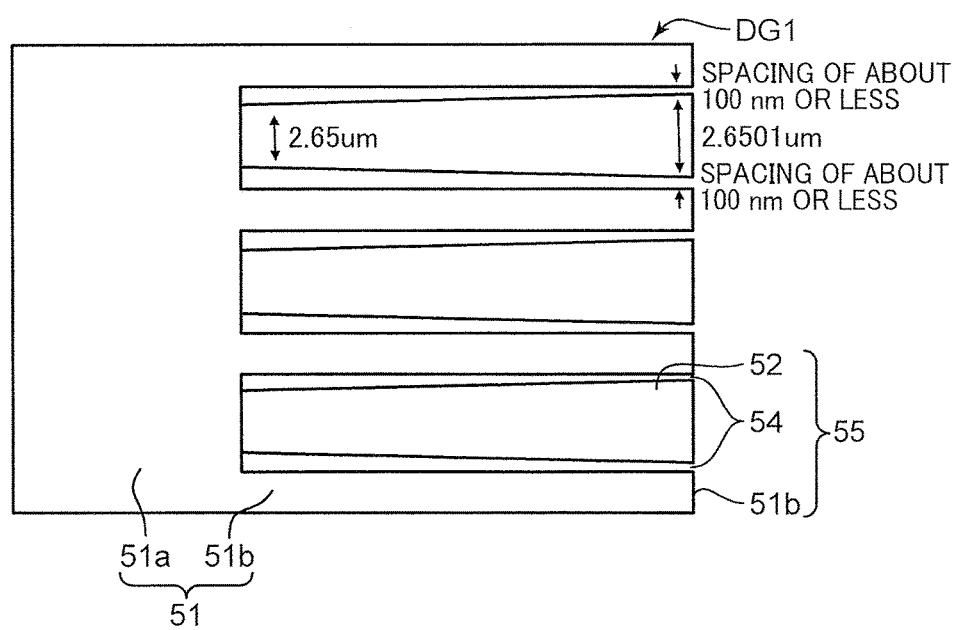
FIG. 7 is a partial sectional view of an X-ray metal grating structure as an inventive example.
Figure 8:
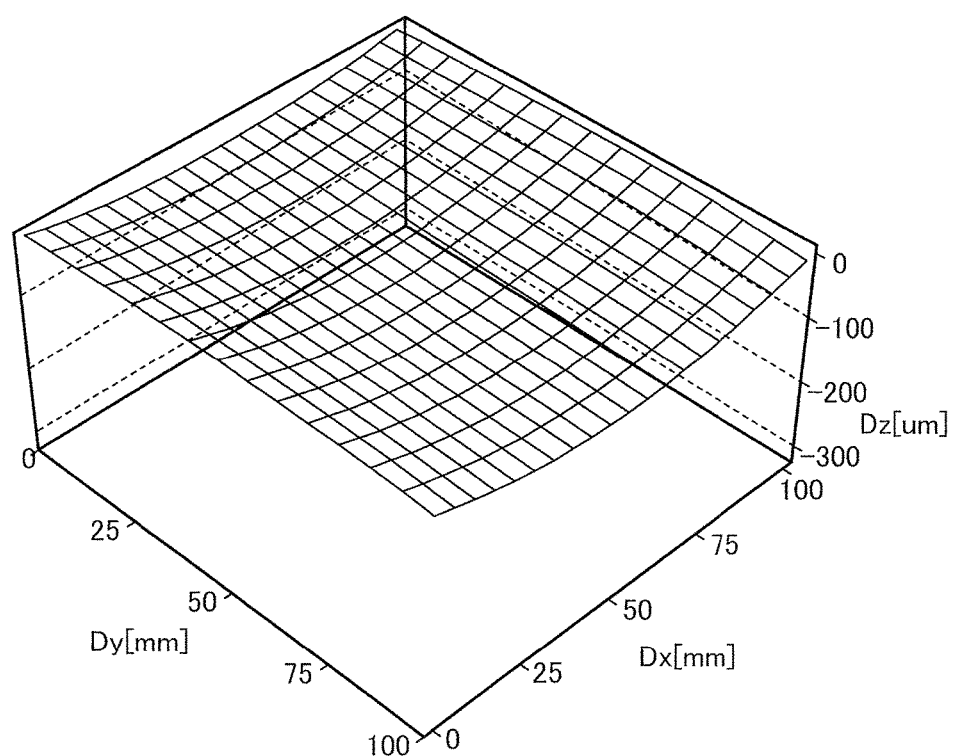
FIG. 8 is a contour line diagram depicting an undulation state of a back surface of the X-ray metal grating structure as the inventive example.
Figure 10A:
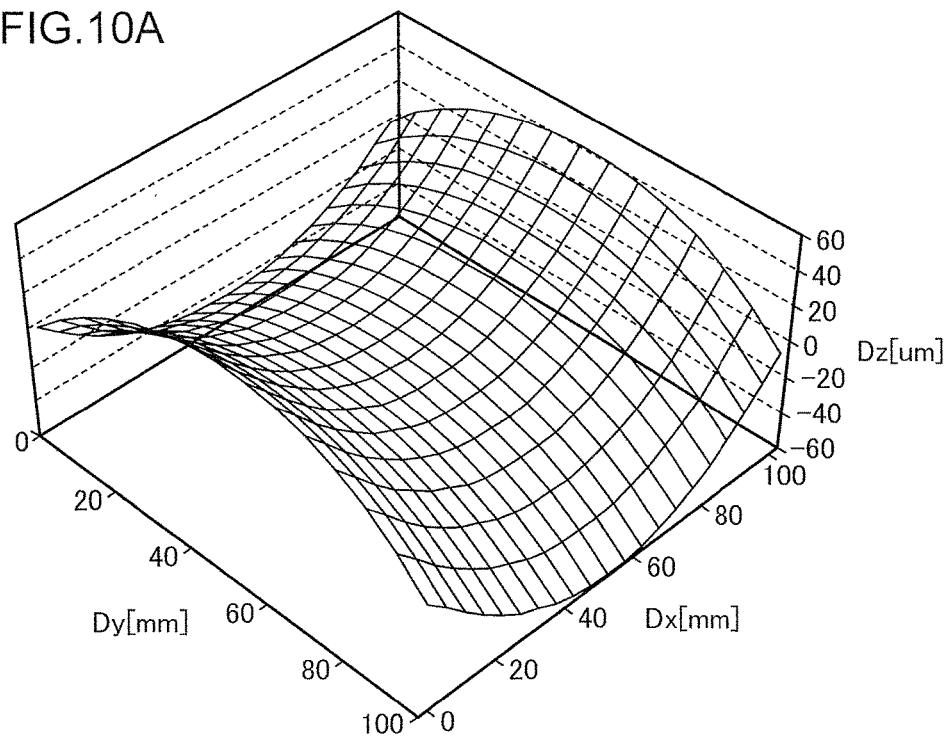
FIG. 10 is a diagram illustrating a state after an on-non-bottom-surface insulation layer forming step in the X-ray metal grating structure as the comparative example.
Figure 10B:
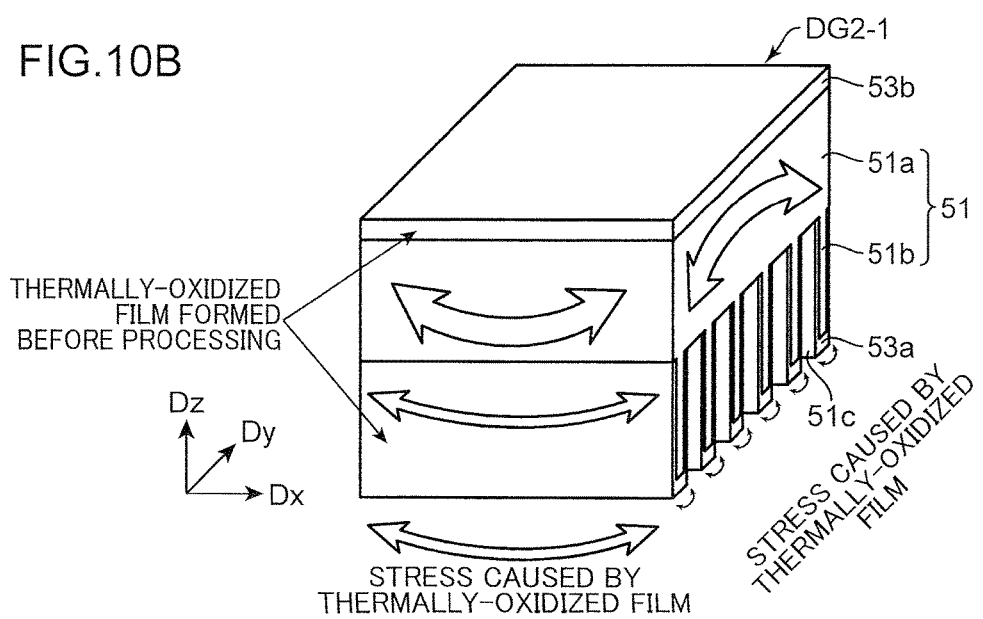
Figure 11A:
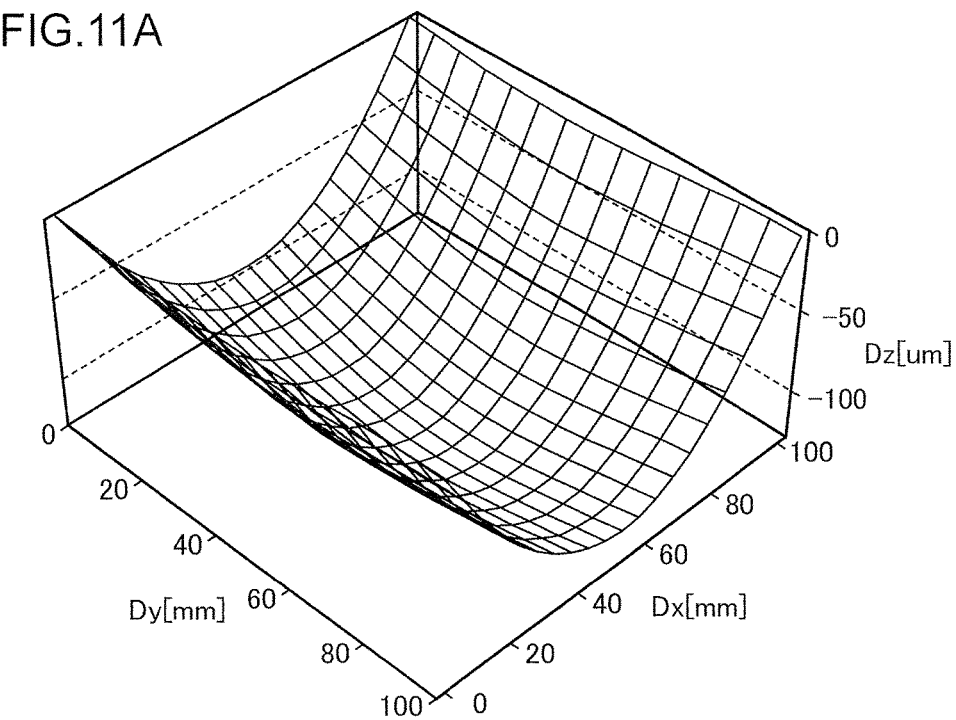
FIG. 11 is a diagram illustrating a state after removing an insulation layer on a back surface of the X-ray metal grating structure as the comparative example, in order to implement an electroforming step.
Figure 11B:
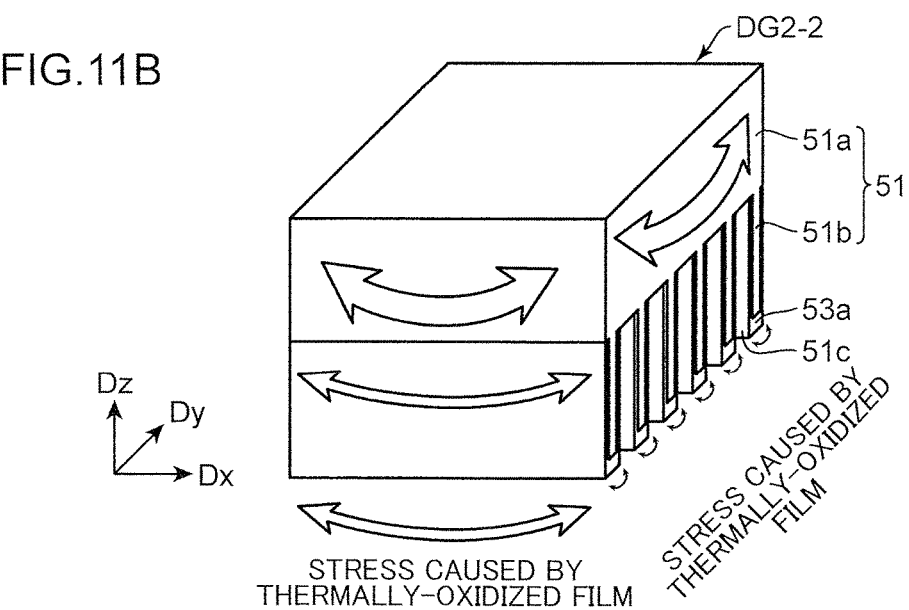
Figure 12A:
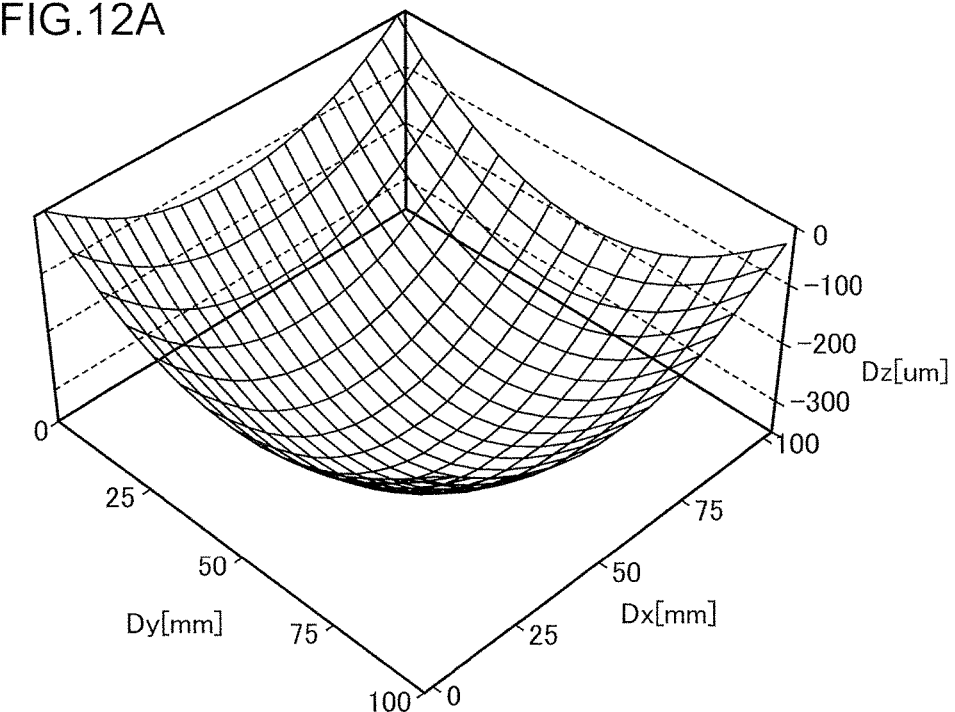
FIG. 12 is a diagram illustrating a state after the electroforming step, in the X-ray metal grating structure as the comparative example.
Figure 12B:
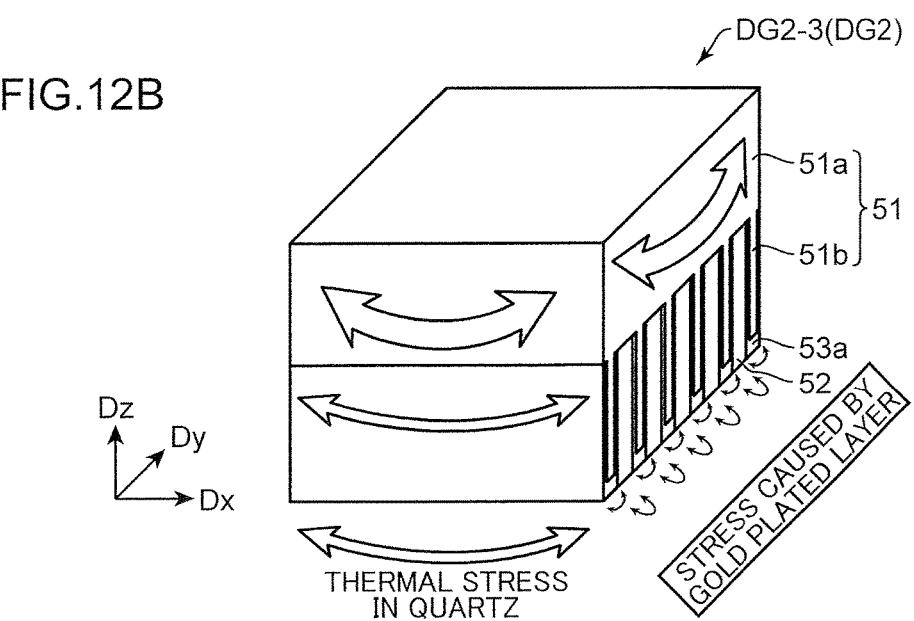

FIG. 7 is a partial sectional view of an X-ray metal grating structure as an inventive example. FIG. 8 is a contour line diagram depicting an undulation state of a back surface of the X-ray metal grating structure as the inventive example. FIG. 9 is a partial sectional view of an X-ray metal grating structure as a comparative example. FIG. 10 is a diagram illustrating a state after the on-non-bottom-surface insulation layer forming step in the X-ray metal grating structure as the comparative example. FIG. 11 is a diagram illustrating a state after removing an insulation layer on a back surface of the X-ray metal grating structure as the comparative example, in order to implement the electroforming step. FIG. 12 is a diagram illustrating a state after the electroforming step, in the X-ray metal grating structure as the comparative example. In FIGS. 10A to 12B, FIG. 10A, FIG. 11A and FIG. 12A are a contour line diagram depicting an undulation state of a back surface, and FIG. 10B, FIG. 11B and FIG. 12B depict a configuration of the X-ray metal grating structure as the comparative example, during a production process.

As depicted in FIG. 7 and FIG. 9, an X-ray metal grating structure DG1 (DG2) as the inventive example (comparative example) includes a grating region 55 (55') having a periodic structure of a silicon structural portion 51b (51b) and a gold remaining portion 52 (52). The grating region 55 (55') has a pitch P of about 5.3 μm, and a thickness (depth) of about 100 μm. The silicon structural portion 51b (51b) has a width of about 2.65 μm, and the gold remaining portion 52 (52) has a width of about 2.65 μm. The X-ray metal grating structure DG2 as the comparative example has an about 100 nm-thick insulation film (silicon oxide film) 53a, between the silicon structural portion 51b and the gold remaining portion 52, whereas the X-ray metal grating structure DG1 as the inventive example has an air gap formed between the silicon structural portion 51b and the gold remaining portion 52 to provide a spacing of about 100 nm or less therebetween, by removing the about 100 nm-thick insulation film (silicon oxide film) 53a of the X-ray metal grating structure DG2 as the comparative example.

The X-ray metal grating structure DG2 as the comparative example is formed by the production method described in the aforementioned Patent Literatures 1 and 2. Specifically, a 6 inch-diameter (φ6 inch) silicon wafer 51 is preliminarily prepared as the silicon substrate 51, and then a resist layer is formed on a principal surface of the silicon substrate 52 (resist layer forming step). Then, the resist layer is patterned and the patterned portion of the resist layer is removed (patterning step). Then, a portion of the silicon substrate 51 corresponding to the removed portion of the resist layer is etched by dry etching to thereby form a recess 51c having a given depth (etching step), and then an insulation layer 53a is formed on an inner surface of the recess 51c of the silicon substrate 51 (insulation layer forming step). Then, a portion of the insulation layer 53a formed on a bottom of the recess 51c is removed (removal step), and then voltage is applied across the silicon substrate 51 to perform an electroforming process to thereby fill the recess 51c with gold 52 (electroforming step). In the electroforming step, before implementing the electroforming process, an insulation layer 53b formed on a back surface of the silicon substrate 51 after being subjected to the removal step is removed to ensure an electrical connection (conduction) between a power supply and the silicon substrate 51. The back surface is a surface opposed to a surface of the silicon substrate 51 (51) subjected to the resist layer forming step to the removal step, i.e., a surface opposed to a surface of the silicon substrate 51 (51) on the side of which the grating region 55 (55') is formed.

As depicted in FIG. 10B, in a state after the insulation layer forming step in the above production process, a grating structure DG2-1 which is an intermediate product of the X-ray metal grating structure DG2 as the comparative example has: a plate-or layer-shaped base plate portion 51a along the plane Dx-Dy; a plurality of plate-or layer-shaped structural portions (wall portions) 51b along the plane Dx-Dz, which are formed on the base plate portion 51a by providing, in the silicon substrate 51; a plurality of plate-or layer-shaped recesses 51c along the plane Dx-Dz orthogonal to the plane Dx-Dy; insulation films (insulation layers) 53a, 53b formed, respectively, on an inner surface of each of the plurality of recesses 51c, and a surface of the base plate portion 51a (a back surface of the silicon substrate 51).

For example, each of the insulation films 53a, 53b is a silicon oxide film, and formed, for example, by a thermal oxidation process. As mentioned above, the thermal expansion coefficient of the silicon is about $2.6 \times 10^{-6}/°$ C. (/K), whereas the thermal expansion coefficient of the silicon oxide film is about $0.7 \times 10^{-6}/°$ C. (/K). In the thermal oxidation process, the silicon substrate 52 formed with the recesses 51c and the structural portions (wall portions) 51b is thermally oxidized at extremely high temperatures (e.g., about 800 to 1100° C.), and then returned to normal temperature. Therefore, due to a difference in thermal expansion coefficient between the silicon and the silicon oxide film, the silicon largely shrinks as compared to the silicon oxide film. As a result, qualitatively, the following deformation occurs. In this regard, FIGS. 10A, 11A and 12A are diagrams depicting results of measurement about flatness, and generally illustrating a tendency of deformation in each step.

In the grating structure DG2-1 depicted in FIG. 10B, when viewed along the plane Dx-Dz, the silicon oxide film 53a is a continuous film in the direction Dx, so that it contributes to the deformation, in a relationship between a thickness of the insulation film 53b in the direction Dz, and a thickness of the insulation film 53a in the direction Dz (a thickness (=height H) of the insulation film 53a formed on side surfaces of each of the structural portions (wall portions) 51b, in the direction Dz). The thickness (=height H) of the insulation film 53a in the direction Dz is fairly larger than the thickness of the insulation film 53b in the direction Dz (the thickness of the insulation film 53a in the direction Dz» the thickness of the insulation film 53b in the direction Dz), so that a portion of the base plate portion 51a on the side of the structural portions 51a formed with the insulation film 53a having a relatively large thickness in the direction Dz is less likely to shrink (the insulation layer 53a composed of the thick silicon oxide film prevents shrinkage of the silicon), whereas a portion of the base plate portion 51a on the side of the insulation film 53b having a relatively small thickness in the direction Dz is more likely to shrink, resulting in warp deformation in the direction Dz.

On the other hand, when viewed along the plane Dy-Dz, a thickness of the insulation film 53b in the direction Dz and a thickness of the insulation film 53a in the direction Dz (a thickness of the insulation film 53a formed on tops of the structural portions (wall portions) 51b, in the direction Dz) are approximately equal to each other. However, in the direction Dy, the insulation film 53b is a continuous film, whereas the insulation film 53a is discontinuous (respective portions of the insulation film 53a formed on the tops of the structural portions (wall portions) 51b are intermittent or discontinuous), so that a portion of the base plate portion 51a on the side of the structural portions 51a formed with the insulation film 53a having the discontinuous tops is weak in terms of a force acting to prevent shrinkage of the silicon, as compared to a portion of the base plate portion 51a on the side of the continuous insulation film 53b, resulting in warp deformation in the direction −Dz.

Thus, as depicted in FIG. 10A, the back surface of the grating structure DG2-1 (back surface of the silicon substrate 51) undulates in a saddle shape, wherein a difference between a highest position and a lowest position with respect to a reference plane Dx-Dy (where Dz=0) is about 120 μm. Thus, flatness of the grating DG2-1 (silicon substrate 51) is deteriorated.

Before implementing the electroforming process in the electroforming step of the aforementioned production process, the insulation layer 53b formed on the back surface of the base plate portion 51a is removed from the grating structure DG2-1 so as to ensure an electrical connection (conduction) between the power supply and the silicon substrate 51. As a result, the grating structure DG2-1 depicted in FIG. 10B is formed as a grating structure DG2-2 which is an intermediate product of the X-ray metal grating structure DG2 as the comparative example. This makes it possible to eliminate a stress causing bulge in the direction Dz (or depression in the direction −Dz) which would otherwise be caused by the silicon oxide film 53b formed on the back surface of the base plate portion 51a. Thus, as depicted in FIG. 11A, the back surface of the grating structure DG2-2 (back surface of the silicon substrate 51) undulates in a curved-surface shape depressed in the direction −Dz, like a part of a cylindrical surface, wherein a difference between a highest position and a lowest position with respect to the reference plane Dx-Dy (where Dz=0) is about 100 μm. Thus, flatness of the grating DG2-2 is improved as compared to the grating DG2-1 depicted in FIG. 10B.

In the electroforming step in the aforementioned production process, a gold portion 52 grows from the bottom of each of the recesses 51c toward an opening of the recess 51c (bottom-up growth). The present inventor found a phenomenon that, during the course of this growth, the gold portion 52 grows such that it expands in the width direction (Dy direction) to an extent slightly greater than a width of the recess 51c as a space to be filled by the electroforming process, and a width of a bottom end thereof becomes slightly greater than a width of a top end (adjacent to the opening of the recess) thereof. In this way, the recesses 51s in the grating structure DG2-2 are filled with the gold 52 growing therein. Thus, in a state after this electroforming step, the grating structure DG2-2 depicted in FIG. 11B is formed as a grating structure DG2-3 depicted in FIG. 12B, i.e., the X-ray metal grating structure DG2 as the comparative example. Due to the above widthwise expansion of the gold portion 52, the deformation in the direction Dz is further increased, so that the grating structure DG2 (DG2-3) is deformed as depicted in FIG. 12A. As a result, as depicted in FIG. 12A, the back surface of the grating structure DG2 (back surface of the silicon substrate 51) undulates in a bowl (tea cup) shape, wherein a difference between a highest position and a lowest position with respect to the reference plane Dx-Dy (where Dz=0) is about 350 μm. Thus, flatness of the grating DG2 (silicon substrate 51) is further deteriorated. Further, the maximum value of strain in the grating structure DG2-1 is about 120 μm, as mentioned above, whereas the maximum value of strain in the grating structure DG2 is about 350 μm, as mentioned above. That is, a stress caused by the widthwise expansion of the gold portion 52 (electroforming stress) is greater than a stress caused by the silicon oxide film 53a, 53b (thermal stress). Estimating the electroforming stress in disregard of the thermal stress and based on the above dimensions, a strain of about 250 μm due to the electroforming stress (in FIG. 12A, while a strain of about 350 μm occurs at a maximum in a diagonal direction in a quadrangle, 100 mm on a side, a strain of about 250 μm occurs at a maximum in a side direction in the quadrangle) can occur under a condition that, when a width of the bottom end is 2.65 μm, a width of the top is about 2.6501 μm, as depicted in FIG. 9. That is, in order to produce a strain of about 250 μm due to the electroforming stress, a required dimensional difference in the width direction between the bottom end and the top end of the gold portion 52 is only 100 pm.

As above, due to thermal stress due to the silicon oxide film 53a formed on a surface of each of the plurality of structural portions 51b and thermal stress due to the gold portion 52 formed in each of the plurality of recesses 51, the X-ray metal grating structure DG2 as the comparative example strains as depicted in FIG. 12A, and thus its flatness is deteriorated.

In the X-ray metal grating structure DG2 as the inventive example depicted in FIG. 7, with respect to the X-ray metal grating structure DG2 as the comparative example depicted in FIGS. 9 and 12B, the silicon oxide film 53a is removed at least in a region formed on the inner surface of each of the plurality of recesses 51c (wall surfaces (side surfaces) of each of the structural portions 51b). In the X-ray metal grating structure DG2 as the inventive example, a portion of the silicon oxide film 53a formed on respective tops of the plurality of structural portions 51b is also removed. Thus, the thermal stress due to the silicon oxide 53a formed on the surface of each of the plurality of structural portions 51b is first resolved. The thickness of the silicon oxide film 53a is greater than the widthwise expansion of the gold portion 52 (e.g., when the thickness of the silicon oxide film 53a is about 100 nm, the widthwise expansion of the gold portion 52 is about 100 pm, i.e., "thickness of the silicon oxide film 53a">"widthwise expansion of the gold portion 52"), so that the electroforming stress due to the gold portion 52 formed in each of the plurality of recesses 51c is absorbed by the air gap formed between corresponding ones of the structural portion 51b and the gold portions 52, by removing the silicon oxide film 53a. As a result, as depicted in FIG. 8, although a back surface (of the silicon substrate 51) of the X-ray metal grating structure DG as the inventive example has a curved-surface slightly depressed in the direction −Dz, like a part of a cylindrical surface, the maximum strain is reduced from about 350 μm to about 30 μm, and its flatness is improved as compared to the X-ray metal grating structure DG2 as the comparative example, i.e., the back surface becomes approximately flat.

Next, another embodiment of the present invention will be described.

Second Embodiment; X-ray Metal Grating Unit

In many cases, an X-ray metal grating structure DG is produced using a silicon wafer (silicon substrate) capable of being fabricated using microfabrication techniques which have been almost established, as mentioned above. From a viewpoint of easiness in sourcing, sourcing cost and others, the silicon wafer is preferably a commonly-used 6 inch-diameter (φ6 inch) type. An X-ray metal grating structure DG fabricatable from such a 6 inch-diameter slicing wafer has a square shape, about 10 cm on a side (□ about 10 cm), and a grating area of □ 10 cm or less. An X-ray metal grating unit DGU according to the second embodiment is directed to resolving restrictions on the grating area.

Figure 13:
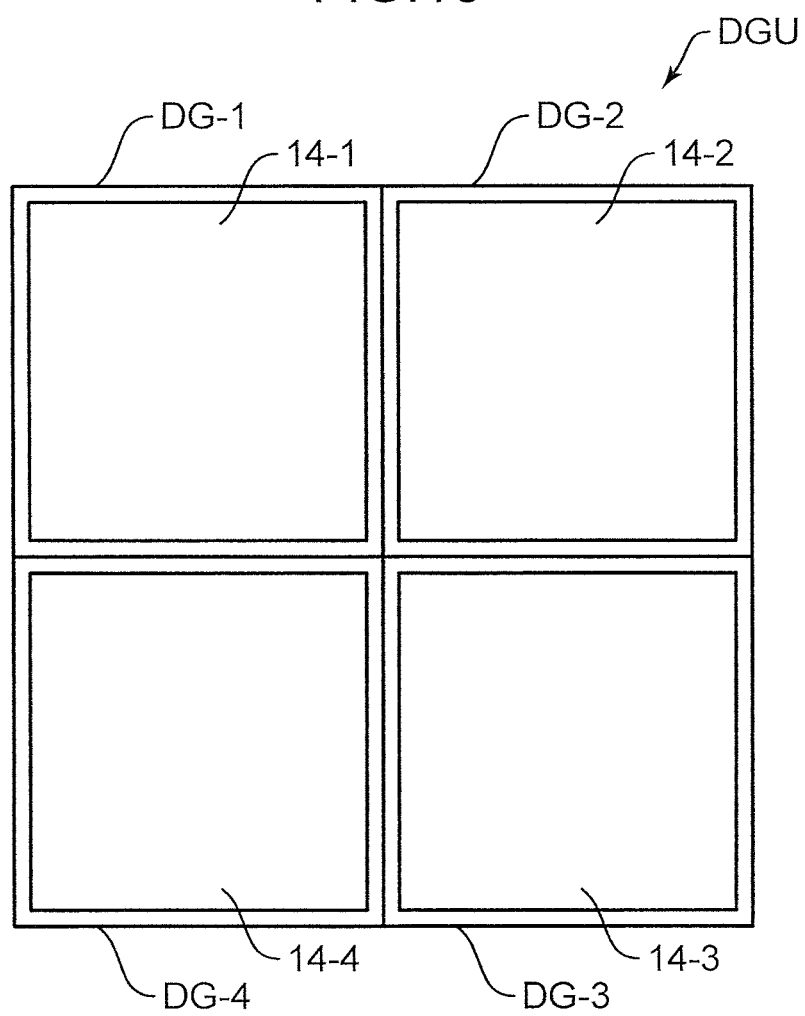
FIG. 13 is a diagram depicting a configuration of an X-ray metal grating unit according to a second embodiment.

FIG. 13 is a diagram depicting a configuration of the X-ray metal grating unit according to the second embodiment. As depicted in FIG. 13, the X-ray metal grating unit DGU according to the second embodiment includes a plurality of X-ray metal grating structures DG arranged to form one grating plane, wherein at least one of the plurality of X-ray metal grating structures DG is composed of the X-ray metal grating structure DG according to the first embodiment.

More specifically, in the embodiment depicted in FIG. 13, the X-ray metal grating unit DGU has four X-ray metal grating structures DG according to the first embodiment. The four X-ray metal grating structures DG according to the first embodiment are arranged in two linear and independent directions, more specifically, in the embodiment illustrated in FIG. 13, in two mutually orthogonal directions and in a 2-row×2-column matrix pattern, to allow four grating planes 14-1 to 14-4 to form one grating planes. That is, in a first direction (direction Dy) with respect to an X-ray metal grating structure DG-1 disposed at a 1st row and 1st column position, an X-ray metal grating structure DG-2 is disposed at a 1st row and 2nd column position, in adjacent relation to the X-ray metal grating structure DG-1, in such a manner that one peripheral side (one of two ends opposed in the direction Dy) thereof comes into contact with one peripheral side of the X-ray metal grating structure DG-1. In a second direction (direction Dx) orthogonal to the first direction (direction Dy) with respect to the X-ray metal grating structure DG-1, an X-ray metal grating structure DG-4 is disposed at a 2nd row and 1st column position, in adjacent relation to the X-ray metal grating structure DG-1, in such a manner that one peripheral side (one of two ends opposed in the direction Dx) thereof comes into contact with one peripheral side of the X-ray metal grating structure DG-1. Further, in an orthogonal direction with respect to the X-ray metal grating structure DG-1, an X-ray metal grating structure DG-3 is disposed at a 2nd row and 2nd column position, in adjacent relation to the X-ray metal grating structure DG-2 and the X-ray metal grating structure DG-4, in such a manner that one peripheral side (one of two ends opposed in the direction Dx) thereof comes into contact with one peripheral side of the X-ray metal grating structure DG-2, and another peripheral side (one of two ends opposed in the direction Dy) thereof comes into contact with one peripheral side of the X-ray metal grating structure DG-4.

In the second embodiment, there is provided an X-ray metal grating unit DGU including the X-ray metal grating structure DG according to the first embodiment, wherein it is possible to obtain a grating surface greater than a grating surface of the one X-ray metal grating structure DG. Particularly, in the case where the X-ray metal grating structure DG is used in an X-ray diagnostic device, in connection with a target area to be diagnosed once, it is necessary to ensure a certain level of size, e.g., a square, 20 cm or more on a side (□ 20 cm or more). The X-ray metal grating unit DGU according to the second embodiment can meet such a need of the X-ray diagnostic device.

Next, two other embodiments of the present invention will be described.

Third and Fourth Embodiments: Talbot Interferometer and Talbot-Lau Interferometer In a refraction grating used in an X-ray Talbot interferometer or Talbot-Lau interferometer, it is necessary that a plurality of structural portions are periodically provided with a period of several μm to several ten μm. For this reason, the production method for the X-ray metal grating structure DG according to this embodiment (including any modification thereof) is suitable for production of a metal grating structure used in an X-ray Talbot interferometer or Talbot-Lau interferometer having such micro-sized periodical structural portions. The following description will be made about an X-ray Talbot interferometer or Talbot-Lau interferometer using an X-ray metal grating structure DG produced by the above production method, or the X-ray metal grating unit DGU according to the second embodiment, including a plurality of the X-ray metal grating structures DG.

Figure 14:
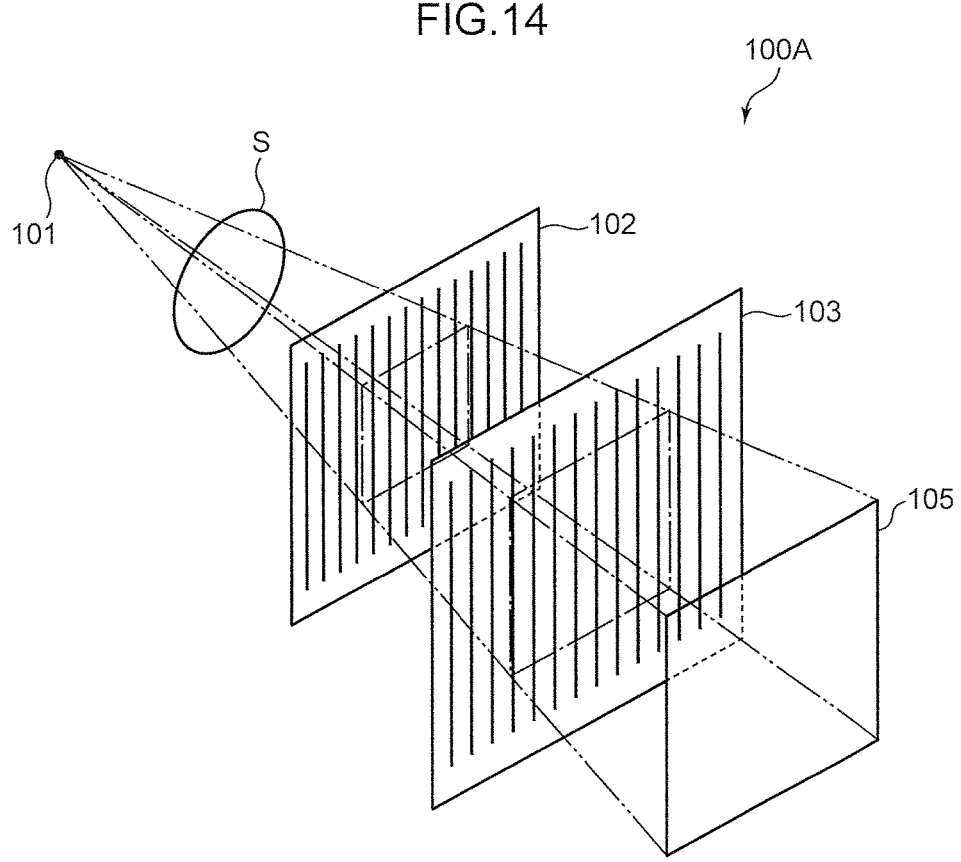
FIG. 14 is a perspective view depicting a configuration of an X-ray Talbot interferometer according to a third embodiment.
Figure 15:
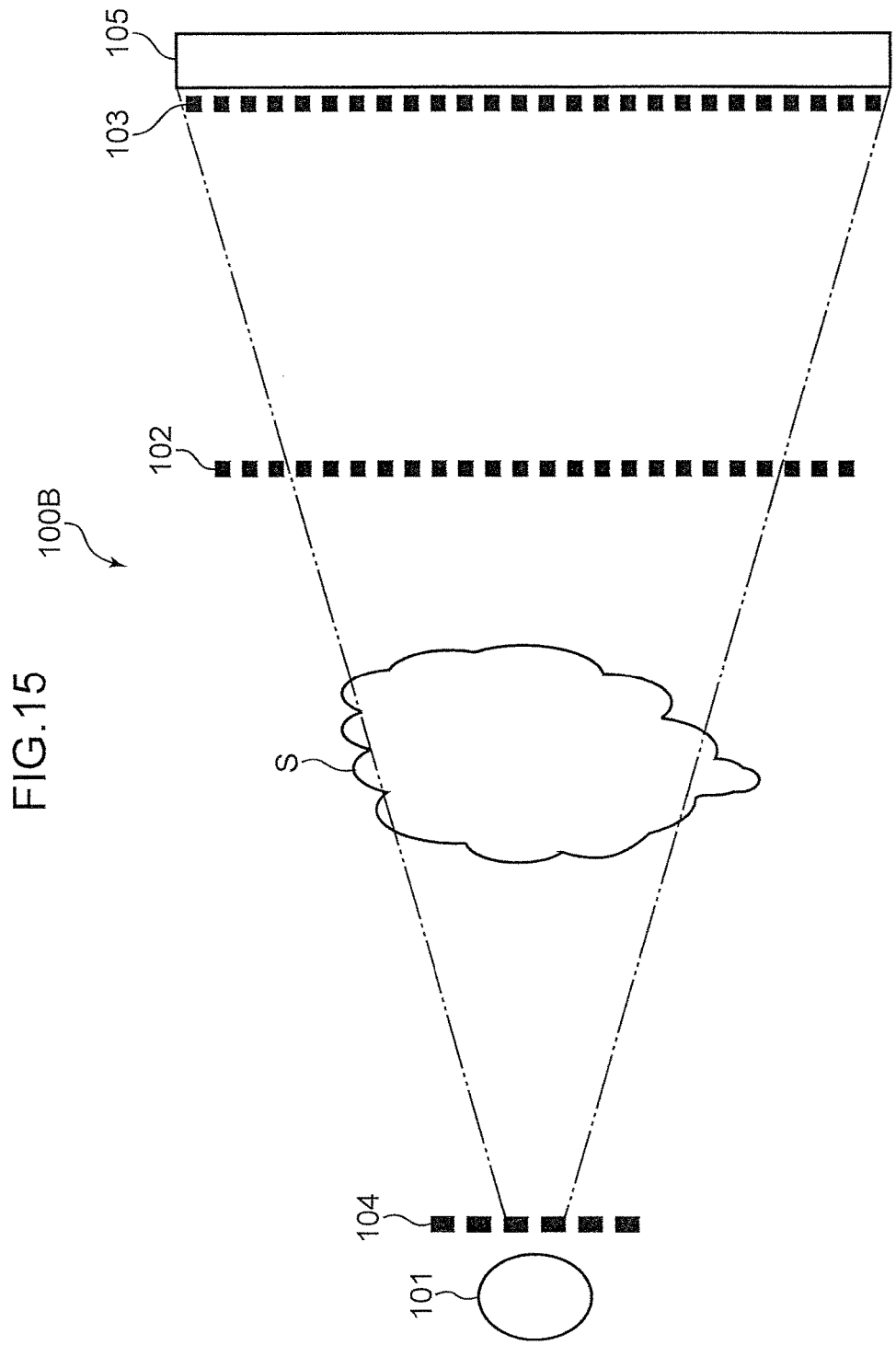
FIG. 15 is a top view depicting a configuration of an X-ray Talbot-Lau interferometer according to a fourth embodiment.

FIG. 14 is a perspective view depicting a configuration of an X-ray Talbot interferometer according to a third embodiment. FIG. 15 is a top view depicting a configuration of an X-ray Talbot-Lau interferometer according to a fourth embodiment.

As depicted in FIG. 14, the X-ray Talbot interferometer 100A according to the third embodiment includes: an X-ray source 101 configured to radiate X-rays having a given wavelength; a first diffraction grating 102 which is a phase type configured to diffract the X-rays radiated from the X-ray source 101; and a second diffraction grating 103 which is an amplitude type configured to diffract the X-rays diffracted by the first diffraction grating 102 to thereby form an image contrast, wherein the first and second diffraction gratings 102, 103 are set to satisfy conditions for constructing an X-ray Talbot interferometer. The X-rays having an image contrast generated by the second diffraction grating 103 are detected, for example, by an X-ray image detector 105 operable to detect X-rays.

In the X-ray Talbot interferometer 100A, at least one of the first diffraction grating 102 and the second diffraction grating 103 has the aforementioned X-ray metal grating structure DG (including any modification thereof), or the aforementioned X-ray metal grating unit DGU. At least one of the first diffraction grating 102 and the second diffraction grating 103 may be produced by the aforementioned production method. In this case, it becomes possible to produce a more flat diffraction grating usable in the X-ray Talbot interferometer 100A.

The conditions for constructing the Talbot interferometer 100A are expressed by the following formulas 1, 2. The formula 2 is based on an assumption that the first diffraction grating 102 is a phase-type diffraction grating.

$$l=\lambda/(a/(L+Z1+Z2)) \quad \text{formula (1)}$$

$$Z1=(m+1/2)\times(d^2/\lambda) \quad \text{formula (2),}$$

where: $l$ denotes a coherence length; $\lambda$ denotes a wavelength of X-rays (generally, center wavelength); $a$ denotes an aperture diameter of the X-ray source 101 in a direction approximately orthogonal to a diffraction member of a diffraction grating; L denotes a distance from the X-ray source 101 to the first diffraction grating 102; Z1 denotes a distance from the first diffraction grating 102 to the second diffraction grating 103; Z2 denotes a distance from the second diffraction grating 103 to the X-ray image detector 105; m denotes an integer; and d denotes a period of a diffraction member (a period of a diffraction grating, a grating constant, a distance between centers of adjacent diffraction members, or the pitch P).

In the X-ray Talbot interferometer 100A having the above configuration, X-rays are radiated from the X-ray source 101 toward the first diffraction grating 102. The radiated X-rays produce a Talbot effect through the first diffraction grating 102 to thereby form a Talbot image. The Talbot image forms an image contrast having moire fringes by an action received through the second grating 103. Then, the image contrast is detected by the X-ray image detector 105.

The Talbot effect means that, upon incidence of light onto the diffraction grating, an image identical to the diffraction grating (a self image of the diffraction grating) is formed at a position away from the diffraction grating by a certain distance, wherein the certain distance is called "Talbot distance L" and the self image is called "Talbot image". In the case where the diffraction grating is a phase-type diffraction grating, the Talbot distance L becomes Z1 (L=Z1) as expressed by the formula 2. The Talbot image appears as a reverted image when the Talbot distance is equal to an odd multiple of L (=(2 m+1), where each of L and m is an integer), and appears as a normal image when the Talbot distance is equal to an even multiple of L (=2 mL).

In the case, when a subject S is disposed between the X-ray source 101 and the first diffraction grating 102, the moire fringes are modulated by the subject S, and an amount of the modulation is proportional to an angle at which X-rays are bent by a refraction effect arising from the subject S. Thus, the subject S and an internal structure of the subject S can be detected by analyzing the moire fringes.

In the Talbot interferometer 100A configured as depicted in FIG. 14, the X-ray source 101 is a single spot light source (spot wave source). Such a single spot light source can be constructed by additionally providing a single slit plate formed with a single slit. X-rays radiated from the X-ray source 101 pass through the single slit of the single slit plate, and is radiated toward the first diffraction grating 102 through the subject S. The slit is an elongate rectangular opening extending in one direction.

On the other hand, as depicted in FIG. 15, a Talbot-Lau interferometer 100B is constructed in such a manner that it includes: an X-ray source 101; a multi-slit plate 104; a first diffraction grating 102; and a second diffraction grating 103. Specifically, the Talbot-Lau interferometer 100B is constructed in such a manner that it comprises, in addition to the Talbot interferometer 100A depicted in FIG. 14, the multi-slit plate 104 having a plurality of slits formed in parallel relation, on an X-ray radiation side of the X-ray source 101.

The multi-slit plate 104 may be the X-ray metal grating structure DG produced by the aforementioned production method or the aforementioned X-ray metal grating unit DGU. When the multi-slit plate 104 is produced by the aforementioned production method, it becomes possible to produce a more flat diffraction grating usable in the X-ray Talbot-Lau interferometer 100B.

When the Talbot-Lau interferometer 100B is used, an X-ray dose irradiated toward the first diffraction grating 102 through the subject S is increased, as compared to the Talbot interferometer 100A, so that it becomes possible to obtain better moire fringes.

Next, an additional embodiment of the present invention will be described.

Fifth Embodiment; X-ray Imaging Device

The X-ray metal grating structure DG and the X-ray metal grating unit DGU are utilizable in a variety of optical devices, and suitably used, for example, in an X-ray imaging device. In particular, an X-ray imaging device using an X-ray Talbot interferometer is one phase contrast method designed to handle X-rays as waves and detect a phase shift occurring when X-rays penetrates through a subject, to obtain a transmission image of the subject, so that it has an advantage of being able to expect to improve sensitivity about 1,000 times, as compared to an absorption contrast method designed to obtain an image by utilizing differences in magnitudes of X-ray absorption by a subject as contrast, thereby reducing an X-ray dose, for example, from $\frac{1}{100}$ to $\frac{1}{1000}$. In this embodiment, an X-ray imaging device equipped with an X-ray Talbot interferometer using the aforementioned X-ray metal grating unit DGU will be described.

Figure 16:
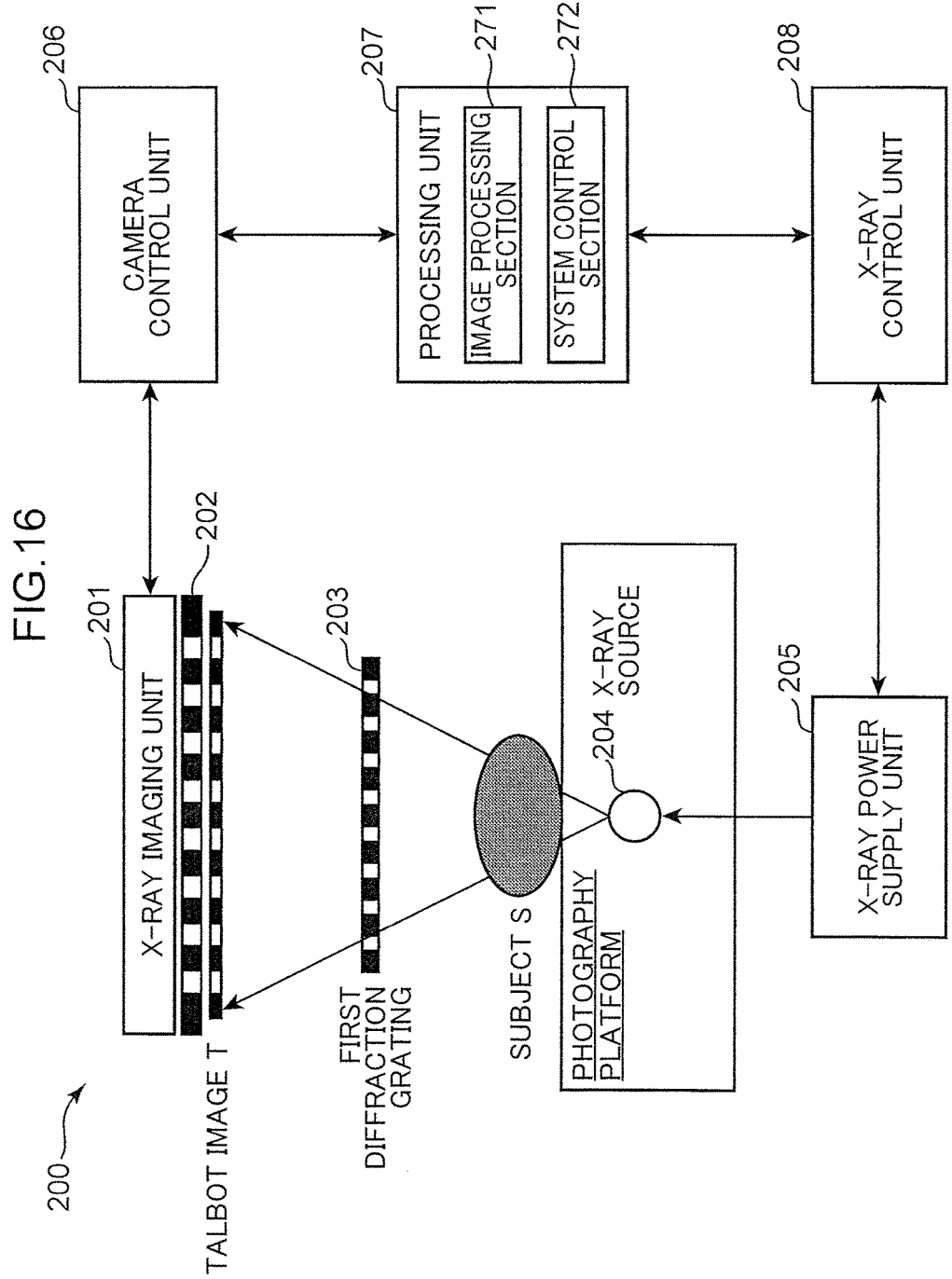
FIG. 16 is an explanatory diagram depicting a configuration of an X-ray imaging device according to a fifth embodiment.

FIG. 16 is an explanatory diagram depicting a configuration of an X-ray imaging device according to a fifth embodiment. In FIG. 16, the X-ray imaging device 200 includes: an X-ray imaging unit 201; a second diffraction grating 202; a first diffraction grating 203; and an X-ray source 204. The X-ray imaging device 200 according to this embodiment further comprises: an X-ray power supply unit 205 for supplying electricity to the X-ray source 204; a camera control unit 206 for controlling an imaging operation of the X-ray imaging unit 201; a processing unit 207 for controlling an overall operation of the X-ray imaging device 200; and an X-ray control unit 208 for controlling an electricity supply operation by the X-ray power supply unit 205 to thereby control an X-ray radiation operation by the X-ray source 204.

The X-ray source 204 is a device operable, in response to receiving electricity supplied from the X-ray power supply unit 205, to radiate X-rays toward the first diffraction grating 203. For example, the X-ray source 204 is a device configured such that a high voltage supplied from the X-ray power supply unit 205 is applied between a cathode and an anode, and electrons released from a filament of the cathode collide with the anode to thereby radiate X-rays.

The first diffraction grating 203 is a diffraction grating configured to produce a Talbot effect by X-rays radiated from the X-ray source 204. For example, the first diffraction grating 203 is composed of the aforementioned diffraction grating unit DGU, in order to take an image of the subject S by a larger area. The first diffraction grating 203 is set to satisfy conditions for producing a Talbot effect, and is a phase-type diffraction grating having a sufficiently coarse grating with respect to a wavelength of X-rays radiated from the X-ray source 204, for example, having a grating constant (a period of a diffraction grating) d of about 20 times or more of the wavelength of the X-rays. The first diffraction grating 203 may be an amplitude-type diffraction grating.

The second diffraction grating 202 is a transmission and amplitude-type diffraction grating disposed at a position away from the first diffraction grating 203 approximately by a Talbot distance L, to diffract X-rays diffracted by the first diffraction grating 203. As with the first diffraction grating 203, the second diffraction grating 202 is composed, for example, of the aforementioned diffraction grating unit DGU.

Preferably, in the first diffraction grating 203, the plurality of X-ray metal grating structures DG constituting the first diffraction grating 203 are arranged along a vertical cylindrical surface having an axis defined by a virtual line passing through a radiation source of the X-ray source 204 as a spot light source, in such a manner that a normal line passing through a center of a light-receiving surface (grating plane) of each of the X-ray metal grating structures DG passes through the radiation source of the X-ray source 204, and the light-receiving surface (grating plane) has contact with the virtual cylindrical surface. Preferably, in the second diffraction grating 202, the plurality of X-ray metal grating structures DG constituting the second diffraction grating 202 are arranged along a vertical cylindrical surface having an axis defined by a virtual line passing through a radiation source of the X-ray source 204 as a spot light source, in such a manner that a normal line passing through a center of a light-receiving surface (grating plane) of each of the X-ray metal grating structures DG passes through the radiation source of the X-ray source 204, and the light-receiving surface (grating plane) has contact with the virtual cylindrical surface.

Preferably, in the first diffraction grating 203, each of the plurality of X-ray metal grating structures DG constituting the first diffraction grating 203 is bent or curved such that a normal line passing through a center of a light-receiving surface (grating plane) of each of the X-ray metal grating structures DG passes through a radiation source of the X-ray source 204 as a spot light source, and the light-receiving surface (grating plane) has contact with a vertical cylindrical surface having an axis defined by a virtual line passing through the radiation source of the X-ray source 204. Preferably, in the second diffraction grating 202, each of the plurality of X-ray metal grating structures DG constituting the second diffraction grating 202 is bent or curved such that a normal line passing through a center of a light-receiving surface (grating plane) of each of the X-ray metal grating structures DG passes through a radiation source of the X-ray source 204 as a spot light source, and the light-receiving surface (grating plane) has contact with a vertical cylindrical surface having an axis defined by a virtual line passing through the radiation source of the X-ray source 204. As above, the X-ray metal grating structure DG itself is curved, so that it becomes possible to reduce the occurrence of a situation where X-rays radiated from the X-ray source 204 undergo so-called "vignetting" at an edge of the X-ray metal grating structure DG (grading adjacent to a side edge). Further, when the X-ray metal grating structure DG itself is bent, the X-ray metal grating structure DG according to the first embodiment is bent from a state in which it has high flatness (flatness accuracy). Thus, it becomes possible to obtain a smooth curved surface (having an approximately uniform curvature at any point on the curved surface), as compared to the case where an X-ray metal grating structure having relatively low flatness due to undulation or the like is bent.

The first diffraction grating 203 may be the aforementioned the X-ray metal grating structure DG, and the second diffraction grating 202 may be the aforementioned the X-ray metal grating structure DG.

The first and second diffraction gratings 203, 202 are set to satisfy conditions for constructing a Talbot interferometer expressed by the aforementioned formulas 1 and 2.

The X-ray imaging unit 201 is a device for imaging an image of X-rays diffracted by the second diffraction grating 202. For example, the X-ray imaging unit 201 is a flat panel detector (FPD) having a two-dimensional image sensor in which a thin film layer containing a scintillator for absorbing X-ray energy and emitting fluorescence is formed on a light receiving surface, or an image intensifier camera including: an image intensifier unit for converting incident photons into electrons by a photoelectric surface, and after doubling the electrons by a micro-channel plate, causing the group of doubled electron to collide with a fluorescent material to generate fluorescence; and a two-dimensional image sensor for imaging output light from the image intensifier unit.

The processing unit 207 is a device for by controlling units of the X-ray imaging device 200 to thereby control the overall operation of the X-ray imaging device 200. For example, the processing unit 207 is constructed in such a manner that it has a microprocessor and peripheral circuits thereof, and functionally includes an image processing section 271 and a system control section 272.

The system control section 272 is operable to transmit and receive control signals with respect to the X-ray control unit 208 to thereby control an X-ray radiation operation of the X-ray source 204 through the X-ray power supply unit 205, and transmit and receive control signals with respect to the camera control unit 206 to thereby control an imaging operation of the X-ray imaging unit 201. Under control of the system control section 272, X-rays are irradiated toward the subject S. Then, a resulting image is taken by the X-ray imaging unit 201, and an image signal is input into the processing unit 207 via the camera control unit 206.

The image processing section 271 is operable to process the image signal generated by the X-ray imaging unit 201, and generate an image of the subject S.

An operation of the X-ray imaging device 200 according to this embodiment will be described. For example, a subject S is placed on a photography platform provided with the X-ray source 204 internally (or on the back thereof), and thereby disposed between the X-ray source 204 and the first diffraction grating 203. When a user (operator) of the X-ray imaging device 200 issues an instruction for imaging the subject S, from a non-depicted operation section, the system control section 272 in the processing unit 207 outputs a control signal to the X-ray control unit 208 for radiating X-rays to the subject S. According to the control signal, the X-ray control unit 208 instructs the X-ray power supply unit 205 to supply electricity to the X-ray source 204, and thus the X-ray source 204 radiates X-rays toward the subject S.

The radiated X-rays passes through the first diffraction grating 203 through the subject S, and is diffracted by the first diffraction grating 203, whereby a Talbot image T as a self image of the first diffraction grating 203 is formed at a position away from the first diffraction grating 203 by a Talbot distance L (=Z1).

The formed Talbot image T of X-rays is diffracted by the second diffraction grating 202, and an image of resulting moire fringes is formed. The image of moire fringes is imaged by the X-ray imaging unit 201 whose parameter such as exposure time is controlled by the system control section 272.

The X-ray imaging unit 201 outputs an image signal indicative of an image of moire fringes, to the processing unit 207 via the camera control unit 206. The image signal is processed by the image processing section 271 in the processing unit 207.

The subject S is disposed between the X-ray source 204 and the first diffraction grating 203. Thus, a phase of X-rays passing through the subject S is shifted from a phase of X-rays which does not pass through the subject S. As a result, X-rays entering the first diffraction grating 203 includes distortion in a wave front thereof, and a Talbot image T is deformed accordingly. Thus, the moire fringes of an image generated by overlapping the Talbot image T and the second diffraction grating 202 undergo modulation by the subject S, and an amount of the modulation is proportional to an angle at which the X-ray is bent by a refraction effect by the subject S. Therefore, the subject S and the internal structure of the subject S can be detected by analyzing the moire fringes. Further, the subject S may be imaged from different angles so as to form a tomographic image of the subject S by X-ray computed tomography (CT).

The second diffraction grating 202 in this embodiment is the X-ray metal grating unit DGU comprising the X-ray metal grating structures DG according to the first embodiment, each having high-aspect ratio metal portions. Thus, it is possible to obtain good moire fringes, thereby obtaining a highly-accurate image of the subject S.

Further, in the case where the X-ray metal grating structure DG of the X-ray metal grating unit DGU is formed by subjecting a silicon wafer to dry etching using a Bosch process, a side surface of each of the recesses becomes more flat, and therefore the second diffraction grating 202 can be formed with a high degree of accuracy. Thus, it is possible to obtain better moire fringes, thereby obtaining a further highly-accurate image of the subject S.

In the above X-ray imaging device 200, a Talbot interferometer is composed of the X-ray source 204, the first diffraction grating 203, and the second diffraction grating 202. Alternatively, a Talbot-Lau interferometer may be constructed by additionally disposing the aforementioned X-ray metal grating structure DG as a multi-slit member on the X-ray radiation side of the X-ray source 204. Based on such a Talbot-Lau interferometer, an X-ray dose to be radiated to the subject S can be increased, as compared to the case where a single slit member is used. This makes it possible to obtain better moire fringes, thereby obtaining a further highly-accurate image of the subject S.

In the above X-ray imaging device 200, a subject S is disposed between the X-ray source 204 and the first diffraction grating 203. Alternatively, a subject S may be disposed between the first diffraction grating 203 and the second diffraction grating 202.

In the above X-ray imaging device 200, an image of X-rays is taken by the X-ray imaging unit 201, and electronic data of the image is obtained. Alternatively, an image of X-rays may be obtained by an X-ray film.

The specification discloses the aforementioned features. The following is a summary of the primary features of the embodiments.

According a first aspect, there is a provided an X-ray metal grating structure which includes a grating-forming workpiece having one surface formed with a grating region in which a plurality of first structural portions mutually having a same shape are periodically provided, wherein: the grating region including the plurality of first structural portions, a second structural portion as a remaining part of the grating region other than the plurality of first structural portions, and an air gap formed between each of the first structural portions and the second structural portion, in such a manner as to provide a given spacing therebetween in a given planar direction on a grating plane of the grating region, and extend along a direction normal to the grating plane of the grating region; and the first structural portion and the second structural portion are made, respectively, of first and second grating region materials each having a respective one of mutually different first and second characteristic values of a given characteristic with respect to X-ray, wherein at least one of the first and second grating region materials is a metal.

The above X-ray metal grating structure has the air gap formed between each of the first structural portions and the second structural portion, so that a stress generated in the X-ray metal grating structure can be absorbed by the air gap. Thus, this X-ray metal grating structure is formed as a grating structure having high flatness (flatness accuracy).

According to another aspect, there is provided an X-ray metal grating structure production method which includes: a grating forming step of forming, on one surface of a grating-forming workpiece made of an electrically-conductive material, a grating region in which a plurality of first structural portions mutually having a same shape are periodically provided via a recess; on-non-bottom-surface insulation layer forming step of forming an insulation layer on a surface of the recess in the grating-forming workpiece, except for a bottom surface of the recess; an electroforming step of applying voltage across the grating-forming workpiece to perform an electroforming process to thereby fill the recess with a metal; and an intervening-insulation layer removing step of removing the insulation layer formed on the surface of the recess in the on-non-bottom-surface insulation layer forming step, at least in a region intervening between the grating-forming workpiece and the metal filled in the electroforming step. Preferably, in the above X-ray metal grating structure production method, the grating forming step includes: a resist layer forming sub-step of firming a resist layer on one principal surface of the grating-forming workpiece; a patterning sub-step of patterning the resist layer using a master pattern appropriate to the grating region, and removing the patterned portion of the resist layer; and an etching sub-step of etching a portion of the grating-forming workpiece corresponding to the removed portion of the resist layer by dry etching to thereby form the recess to have a given depth. Preferably, in the above X-ray metal grating structure production method, the on-non-bottom-surface insulation layer forming step includes: an insulation layer forming sub-step of forming an insulation layer on a surface of the recess of the grating-forming workpiece; and a removal sub-step of removing a portion of the insulation layer formed on a bottom of the recess. More preferably, in the above X-ray metal grating structure production method, the on-non-bottom-surface insulation layer forming step further includes: a surface area-increasing sub-step of further etching a portion of the grating-forming workpiece corresponding to the bottom of the recess exposed by removing, in the removal sub-step, the portion of the insulation layer formed at the bottom of the recess, to thereby increase a surface area of the bottom of the recess, as compared to the surface area before the etching.

In this X-ray metal grating structure production method, the air gap is formed between each of the first structural portions and the second structural portion, in the on-non-bottom-surface insulation layer forming step, so that it becomes possible to absorb a stress generated in X-ray metal grating structure after production, by the air gap. Therefore, the X-ray metal grating structure production method makes it possible to produce an X-ray metal grating structure with higher flatness (flatness accuracy).

In another aspect, in these above X-ray metal grating structure production method, the grating-forming workpiece may be a substrate made of silicon. In this X-ray metal grating structure production method, a substrate made of silicon is used as the grating-forming workpiece, so that it becomes possible to use so-called "silicon fabrication techniques" and thus produce a microstructural grating region with a relatively high degree of accuracy.

In another embodiment of the above X-ray metal grating structure production method, the silicon is n-type silicon. In this X-ray metal grating structure production method, a conductivity type of the silicon is n-type, so that when the silicon substrate is set to a cathode during an electroforming process, a electrons can be given from the silicon substrate to a plating solution to induce precipitation of a metal.

In another aspect, in these above X-ray metal grating structure production method, the intervening-insulation layer removing step includes immersing the grating-forming workpiece in a hydrofluoric acid solution to thereby remove the at least region of the insulation layer intervening between the grating-forming workpiece and the metal filled in the electroforming step. In this X-ray metal grating structure production method, a hydrofluoric acid solution is used, so that it becomes possible to reliably remove the silicon dioxide ($SiO_2$) insulation layer.

In another aspect, in these above X-ray metal grating structure production method, the grating forming step includes forming the recess in the one surface of the grating-forming workpiece by dry etching using a Bosch process to thereby form the grating region. In this X-ray metal grating structure production method, the grating-forming workpiece is etched by dry etching using a Bosch process, so that a side surface of the recess becomes more flat, and thus the X-ray metal grating structure can be formed with a high degree of accuracy.

In another aspect, in these above X-ray metal grating structure production method, the on-non-bottom-surface insulation layer forming step includes forming the insulation layer by a thermal oxidation process or an anodic oxidation process. In this X-ray metal grating structure production method, in the case of forming the insulation layer using the thermal oxidation process, it is possible to form an oxide film which is dense and excellent in adhesion, and relatively easily control a film thickness thereof. In the case of forming the insulation layer using the anodic oxidation process, it is possible to form an oxide film which is dense and excellent in adhesion and film thickness uniformity, and relatively easily control a film thickness thereof. Thus, this X-ray metal grating structure production method can form an insulation layer capable of being densified with a given thickness, while ensuring electrical insulation against an electroforming process in the electroforming step.

In another aspect, in these above X-ray metal grating structure production method, the metal is at least one selected from the group consisting of gold (Au), platinum (Pt), iridium (Ir) and rhodium (Rh). In this X-ray metal grating structure production method, the metal is at least one selected from the group consisting of gold, platinum, iridium and rhodium, which are preferred examples of a metal having a relatively large atomic weight. These metals relatively largely act to X-rays, so that it becomes possible to reduce a depth of the recess. Therefore, this X-ray metal grating structure production method can easily produce a grating structure.

According to another aspect, there is provided an X-ray metal grating structure produced by the above X-ray metal grating structure production method. This provides an X-ray metal grating structure produced by the above X-ray metal grating structure production method According to another aspect, there is provided an X-ray metal grating unit which includes a plurality of X-ray metal grating structures arranged to form one grating plane, wherein at least one of the plurality of X-ray metal grating structures is composed of the aforementioned X-ray metal grating structure. This provides an X-ray metal grating unit comprising a plurality of the aforementioned X-ray metal grating structures, so that it is possible to obtain a grating surface greater than a grating surface of one X-ray metal grating structure.

According to another aspect, there is provided an X-ray imaging device which includes: an X-ray source for radiating X-rays; a Talbot interferometer or Talbot-Lau interferometer configured to be irradiated with X-rays radiated from the X-ray source; and an X-ray imaging element for imaging X-rays from the Talbot interferometer or Talbot-Lau interferometer, wherein the Talbot interferometer or Talbot-Lau interferometer comprises the aforementioned X-ray metal grating structure. This provides an X-ray imaging device comprising the aforementioned X-ray metal grating structure.

This application is based on Japanese Patent Application Serial No. 2013-199968 filed in Japan Patent Office on Sep. 26, 2013, the contents of which are hereby incorporated by reference.

To express the present invention, the present invention has been appropriately and sufficiently described through the embodiments with reference to the drawings above. However, it should be recognized that those skilled in the art can easily modify and/or improve the embodiments described above. Therefore, it is construed that modifications and improvements made by those skilled in the art are included within the scope of the appended claims unless those modifications and improvements depart from the scope of the appended claims.

INDUSTRIAL APPLICABILITY

The present invention can provide an X-ray metal grating structure, an X-ray metal grating structure production method, an X-ray metal grating unit, and an X-ray imaging device.

The invention claimed is:

1. An X-ray metal grating structure comprising a grating-forming workpiece having one surface formed with a grating region in which a plurality of first structural portions are provided,
wherein the grating region comprises: the plurality of first structural portions, a plurality of second structural portions located in a first part of the grating region different from a second part of the grating region where the plurality of first structural portions are located, and at least one air gap located in a third part of the grating region different from the first part and the second part, the at least one air gap being formed between adjacent ones of the first and second structural portions; and
wherein each of the first structural portions and each of the second structural portions are made, respectively, of first and second grating region materials each having a respective one of mutually different first and second characteristic values of a given characteristic with respect to X-ray, wherein at least one of the first and second grating region materials is a metal.

2. An X-ray metal grating structure production method comprising:
a grating forming step of forming, on one surface of a grating-forming workpiece made of an electrically-conductive material, a grating region having a plurality of first structural portions provided via a recess, and a plurality of second structural portions;
on-non-bottom-surface insulation layer forming step of forming an insulation layer on a surface of the recess in the grating-forming workpiece, except for a bottom surface of the recess;
an electroforming step of applying voltage across the grating-forming workpiece to perform an electroforming process to thereby fill the recess with a metal; and
an intervening-insulation layer removing step of forming a gap between adjacent ones of the first structural portions and the second structural portions by removing the insulation layer formed on the surface of the recess in the on-non-bottom-surface insulation layer forming step, at least in a region intervening between the grating-forming workpiece and the metal filled in the electroforming step.

3. The X-ray metal grating structure production method as recited in claim 2, wherein the grating-forming workpiece is a substrate made of silicon.

4. The X-ray metal grating structure production method as recited in claim 3, wherein the silicon is n-type silicon.

5. The X-ray metal grating structure production method as recited in claim 2, wherein the intervening-insulation layer removing step includes immersing the grating-forming workpiece in a hydrofluoric acid solution to thereby remove the at least region of the insulation layer intervening between the grating-forming workpiece and the metal filled in the electroforming step.

6. The X-ray metal grating structure production method as recited in claim 2, wherein the grating forming step includes forming the recess in the one surface of the grating-forming workpiece by dry etching using a Bosch process to thereby form the grating region.

7. The X-ray metal grating structure production method as recited in claim 2, wherein the on-non-bottom-surface insulation layer forming step includes forming the insulation layer by a thermal oxidation process or an anodic oxidation process.

8. The X-ray metal grating structure production method as recited in claim 2, wherein the metal is at least one selected from the group consisting of gold (Au), platinum (Pt), iridium (Ir) and rhodium (Rh).

9. An X-ray metal grating structure produced by the X-ray metal grating structure production method as recited in claim 2.

10. An X-ray metal grating unit comprising a plurality of X-ray metal grating structures arranged to form one grating plane, wherein at least one of the plurality of X-ray metal grating structures is composed of the X-ray metal grating structure as recited in claim 1.

11. An X-ray imaging device comprising:
an X-ray source for radiating X-rays;
a Talbot interferometer or Talbot-Lau interferometer configured to be irradiated with X-rays radiated from the X-ray source; and
an X-ray imaging element for imaging X-rays from the Talbot interferometer or Talbot-Lau interferometer,
wherein the Talbot interferometer or Talbot-Lau interferometer comprises the X-ray metal grating structure as recited in claim 1.

12. An X-ray metal grating unit comprising a plurality of X-ray metal grating structures arranged to form one grating plane, wherein at least one of the plurality of X-ray metal grating structures is composed of the X-ray metal grating structure as recited in claim 9.

13. An X-ray imaging device comprising:
an X-ray source for radiating X-rays;
a Talbot interferometer or Talbot-Lau interferometer configured to be irradiated with X-rays radiated from the X-ray source; and
an X-ray imaging element for imaging X-rays from the Talbot interferometer or Talbot-Lau interferometer,
wherein the Talbot interferometer or Talbot-Lau interferometer comprises the X-ray metal grating structure as recited in claim 9.

* * * * *